(12) United States Patent
Jaehne et al.

(10) Patent No.: US 6,982,353 B2
(45) Date of Patent: Jan. 3, 2006

(54) C2-DISUBSTITUTED INDAN-1-OL COMPOUNDS, THEIR DERIVATIVES, PROCESSES FOR THEIR PREPARATION, AND THEIR USE AS PHARMACEUTICALS

(75) Inventors: Gerhard Jaehne, Frankfurt (DE); Volker Krone, Hofheim (DE); Martin Bickel, Bad Homburg (DE); Matthias Gssel, Hofheim (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 10/231,418

(22) Filed: Aug. 29, 2002

(65) Prior Publication Data

US 2003/0181491 A1 Sep. 25, 2003

(30) Foreign Application Priority Data

Aug. 31, 2001 (DE) .......................... 101 42 663

(51) Int. Cl.
| | |
|---|---|
| C07C 319/00 | (2006.01) |
| C07C 321/00 | (2006.01) |
| C07C 323/00 | (2006.01) |
| C07C 381/00 | (2006.01) |
| C07C 319/14 | (2006.01) |

(52) U.S. Cl. .............................. 568/38; 568/39; 568/44; 568/45; 568/51; 568/52; 568/55; 568/18; 568/27; 568/28

(58) Field of Classification Search ................... 568/38, 568/39, 44, 45, 51, 52, 55, 18, 27, 28
See application file for complete search history.

(56) References Cited

U.S. PATENT DOCUMENTS

| | | | |
|---|---|---|---|
| 3,016,348 A | 1/1962 | Holden | |
| 3,016,349 A | 1/1962 | Oswald | |
| 3,043,824 A | 7/1962 | Oswald | |
| 3,050,564 A | 8/1962 | Oswald | |
| 5,985,913 A | 11/1999 | Williams et al. | |
| 6,005,103 A | 12/1999 | Domagala et al. | |

FOREIGN PATENT DOCUMENTS

| | | |
|---|---|---|
| DE | 2025973 | 1/1980 |
| DE | 19844547 A1 | 3/2000 |
| DE | 19908533 A1 | 8/2000 |
| WO | WO 95/14013 | 5/1995 |
| WO | WO 97/20806 A1 | 6/1997 |
| WO | WO 97/2625 | 7/1997 |
| WO | WO 97/41097 A2 | 11/1997 |
| WO | WO 98/08871 | 3/1998 |
| WO | WO 98/55439 | 12/1998 |
| WO | WO 99/03861 | 1/1999 |
| WO | WO 01/12176 A2 | 2/2001 |
| WO | WO 03/020199 | 3/2003 |
| WO | WO 03/020255 | 3/2003 |
| WO | WO 03/020263 | 3/2003 |
| WO | WO 03/020693 | 3/2003 |
| WO | WO 03/020694 | 3/2003 |
| WO | WO 03/020695 | 3/2003 |
| WO | WO 03/020696 | 3/2003 |

OTHER PUBLICATIONS

CA:56:73337 abs of Journal of Organic Chemistry by Oswald et al 26 pp 3974–80 1961.*
CA:86:170438 abs of Tetrahedron by Szmant et al 32(22) pp 2665–80 1976.*
CA:115:158285 abs of Phosphorus, Sulfur and Silicon and the Related elements by Freer et al 61(1–2) pp 41–8 1991.*
CA:119:270944 abs of Jounal of Organic Chemistry by Lewis et al 58(23) pp 6390–3 1993.*
CA:92:113102 abs of EP 3336 Aug. 1979.*
CA:102:113102 abs of Journal of the Chem Soc. Perkin Trans. 1 by Phialas et al (4) pp 687–95 1984.*
Abou–Hadeed, et al., A 'One–Pot' Anellation Method for the Transformation of Heptalene–4,5–dicarboxylates into Benzo[a]heptalenes, Helvetica Chimica Acta, (1997), 80 (8), 2535–2564.
Baeza, et al., Stereoselective Oxidative Addition of Benzenethiol To Indene In the Presence of Ovoalbumin, Monatshefte fuer Chemie, (1984), 115(11), 1369–1371.
Cambie, et al., Reactions of n2–(2–acylaryl–C,O) tetracarbonylmanganese (I) complexes with some vinyl sulfur compounds, Journal of Organometallic Chemistry (1994), 467 (2), 237–244.
Einbaum, et al., Synthesis and Reactions of Trans–2(2'–Nitrophenylthio)–1–Chloroindane, Phosphorus and Sulfur, (1985), 22(2), 231–240.

(Continued)

*Primary Examiner*—Elvis O. Price
(74) *Attorney, Agent, or Firm*—Julie Anne Knight; Raymond S. Parker, III; Smith, Gambrell & Russell, LLP

(57) ABSTRACT

The present invention is directed to C2-disubstituted indan-1-ol systems of the Formula I,

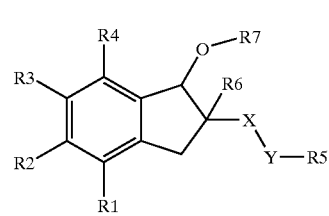

I physiologically acceptable salts and physiologically functional derivatives thereof, and pharmaceutical compositions comprising such compounds, salts, and derivatives, which are useful for reducing weight, for the prophylaxis or treatment of obesity, and for the prophylaxis or treatment of type II diabetes in mammals. The invention is directed also to methods for reducing weight and such treatments and prophylaxis. The invention is directed also to processes for the preparation of such compounds.

6 Claims, No Drawings

OTHER PUBLICATIONS

Ford, et al., Stereochemisry of The Co–oxidation Products of Indene And Thiophenol, Tetrahedron (1958), 4, 325–336.

Ford, et al., The Co–oxidation of Olefins and Mercaptans, Am. Chem. Soc., Div. Petrol. Chem., Preprints (1957), 2(1), 111–122.

Freer, et al., Reaccion De Adicion Oxidativa De Tiofenol Y Ciclopenteno Cooxidation between Thiophenol and Cyclopentene, Boletin de la Sociedad Chilene de Quimica, (1991), 36 (1), 11–16.

Gritsenko, et al., Behavior of Cycloalkenes in Sulfenylchlorination–Dehydrochlorination Reactions, Zhurnal Organicheskoi Khimii, (1984), 20(4), 741–746.

Kerdel, et al., The Role of 12,2–Epoxyindene in the Metabolism of indene in vivo, Biochemical Society Transactions (1978), 6(4), 785–787.

Morris, et al., Fuel Instability Model Studies: The Liquid–Phase Cooxidation of Thiols and Indene by Oxygen, Energy & Fuels (1991), 5(5), 744–748.

Mushrush, et al., Liquid Phase Oxidation Of Thiophenol And Indene By t–Butyl Hydroperoxide And Oxygen, Fuel Science & Technology Int'l, (1988), 6(2), 165–183.

Oswald, Alexis, Organic Sulfur Compounds. III. Co–Oxidation of Mercaptans with Styrenes and Indene, J. Org. Chem., (1961), 26, 842–846.

Oswald, et al., Co–oxidation of Alpha Olefins with Thiols by Molecular Oxygen, Am. Chem. Soc., Div. Petrol. Chem., Preprints (1963), 8(2), B87–B94.

Oswald, et al., Organic Sulfur Compounds. VI. The Effect of Alkylamines on the Course of the Co–Oxidation of Mercaptans and Indene, J. Org. Chem., (1961), 26, 3974–3980.

Oswald, et al., Organic Sulfur Compounds. XIV. Oxidative Addition of Thiol Acids to Unsaturated Hydrocarbons. Cooxidation of Thiolacetic Acid and Indene by Molecular Oxygen, Journal of the American Chemical Society (1964), 86(18), 3791–1795.

Oswald, Alexis, Organic Sulfur Compounds I. Hydroperoxide Intermediates in the Co–oxidation of Mercantans and Olefins, J. Org. Chem., (1959), 24, 443.

Perjessy, et al., Electroreduction of The Enolate–Anions Of Some 2–Arylthio–And–2–Aroxy–1,3–Indandiones. Infrared Spectra And Structure of Reduction Products, Collection of Czechoslovak Chemical Communications, (1972), 37(4), 1160–1165.

Sayo, et al., Studies on Sulfenamides. IX. Anodic Oxidation of N–(o–Nitrophenylthio) alicyclic Amines, Chem. Pham. Bull., (1985), 33(6), 2541–2544.

Scheffler, et al., Investigations on Leaving Group Based Intra–Versus Intermolecular Glycoside Bond Formation, Eur. J. Org. Chem. 2000, 3527–3539.

Scharghi, et al., Phenol–Containing Macrocyclic Diamides as New Catalysts in the Highly Regioselective Conversion of Epoxides of β–Hydroxy Thiocycanates, J. Org. Chem. 2001, 66, 7287–7293.

Sharghi, et al., Sciff–Base Metal (II) Complexes as New Catalysts in the Efficient, Mild and Regioselective Conversion of 1,2–Epoxyethanes to 2–Hydroxethyl Thiocyanates with Ammonium Thiocyanate, Bull. Chem. Soc. Jpn., 76, 137–142 (2003).

Szmant, et al., A New Route to 1,2–Indanedione, Organic Preparations And Procedures Int. (1977), 9(1), 35–38.

Szmant, et al., A New Route to 1,2–Indanedione, Organic Preparations And Procedures Int. (1977), 9(1), 35–38.

Szmant, et al., Intramolecular Hydrogen Bonding in cis–2–Phenylmercaptoindanol, Journal of Organic Chemistry, (1966), 31(7), 2288–2290.

Szmant, et al., Nonstereospecific Oxidative Addition of Benzenethiol to Indene, J. Org. Chem., (1972), 37(3), 447–451.

Szmant, et al., The Thiol–Olefin Co–oxidation (TOCO) Reaction—IV. Temperature Effects on Product Distribution in the TOCO Readtion of Indene And Aromatic Thios, Tetrahedron, (1976), 32(22), 2665–2680.

Szmant, et al., Thiol–Olefin Cooxidation Reaction. 6. A New Convenient Route to 1–Substituted Indenes. Indenone as Dienophile in Diels–Alder Reactions, J. Org. Chem., (1978), 43(9), 1835–1837.

Yadav, et al., InCl3–Catalyzed Highly Regioselective Ring Opening of Epoxides with Thiols, Chemistry Letters 2002, (9), 906–907.

Edwards D. et al., The Oxidation of Alkyl Sulphides, 1954, 3272–3274, J. Chem. Soc.

Lambert P.D. et al., Ciliary Neurotyrophic Factor Activates Leptin–like Pathways and Reduces Body Fat, Without Cachexia or Rebound Weight Gain, Even in Leptin–resistant Obesity, PNAS, 2001, vol. 98, No. 8, 4652–4657.

Maiti A K. et al., Polyethylene Glycol (PEG) 4000 Catalysed Regioselective Nucleophilic Ring Opening of Oxiranes—A New And Convenient Synthesis of beta–Hydroxy Sulfone and beta–Hydroxy Sulifide, Tetrahedron, vol. 50, No, 35, 1994, 10483–10490.

Monteiro Hugo J. et al., A New Synthesis of beta–Keto–Phenylsulfoxides, Tetrahedron Letters, No. 11, 1975, 921–924.

Seebach Dieter et al., Herstellung alpha–thiolierter Carbonylverbindungen 1,2), Chemical Ber., 109, 1976, 1601–1616.

Sviridova A.V. et al., A Method for the Selective Oxidation of Sulfides to Sulfoxides, 1971, 2577–2580, 7, J. Org. Chem.

Tyle Praveen, Iontophoretic Devices for Drug Delivery, Pharmaceutical Research, 1986, vol. 3, No. 6, 318–326.

Venier Clifford G. et al., Peroxytrifluoroacetic Acid. A Convenient Reagent for the Preparation of Sulfoxides and Sulfones, J. Org. Chem, 1982, 47, 3773–3774.

Thompson, Hugh W., Sterochemical Control of Reductions. The Directive Effect of Carbomethoxy vs. Hydroxymethyl Groups in Catalytic Hydrogenation, The Journal of Organic Chemistry, Sep. 10, 1971, vol 36, No. 18, 2577–2581.

Trapani, et al., Reaction of 2,2'–Dithiodianiline with 2–Alkyl–1,3–Diketones, Synthesis and Chemical Behavior of Some 2–Acyl–2H–1,4–Benzothiazines, J. Heterocyclio Chem., 26, 721 (1989).

Bieniarz, et al., A Facile High–Yielding Method for the Conversion of Halides to Mercaptans. *Tetrahedron Letters*, vol. 34, No. 6, pp. 939–942 (1993) (The Bibliography Information), and Abstract of CA 118:212104 from Chemical Abstract CA Plus file (1993).

Freer, et al., Cooxidation Reaction of Indene and Aromatic Thiols in the Presence of Ovalbumin. *Phosphorus, Sulfur, and Silicon*, 1991, vol. 61, pp. 41–48 (The Bibliography Information), and Abstract of CA 115:158285 from Chemical Abstract CA Plus file (1991).

Guy, et al., Pseudohalogen Chemistry. II. Heterolytic addiction of thiocyanogen chloride to symmetrical α–arylalkenes, *J.C.S. Perkins II*, 1973, pp. 1359–1362 (The Bibliography Information), and Abstract of CA 79:136138 from Chemical Abstract CA Plus file (1973).

Martigny, et al., Electrochemical reduction of alpha alpha'–Disubstituted 1,2–diphenylethanes. An example of autocatalyzed cathodic elimination, *J. Electronal Chem.*, 81 (1977) 407–412 (The Bibliography Information) and Abstract of CA 87:183720 from Chemical Abstract CA Plus file (1977).

Martigny, et al., Electrogenerated Anion Radical as Reduction Reagents: An Example of Autocatalyzed Cathodic Elimination, the Bibliography Informatioin and Abstract of CA 91: 165553 from *Chemical Abstract CA* Plus file (1978).

Morishita et al., Reaction of Thiosulfinates with Trihaloacetic Anhydrides. II. Addition of Sulfenyl Trihaloacetates to Olefines, *Tetrahedron*, vol. 37, No. 15, pp. 2539–2546, 1981(The Bibliography Informatiion) and Abstract of CA 96:51749 from Chemical Abstract CA Plus file (1981).

Muecke et al., Inactivation of influenza virus by α–dicarbonyl compounds. The Biliography Information and Abstract of CA 68:1013 from Chemical Abstract CA Plus file (1967) *ABSTRACT ONLY*.

Pearson et al., "The Inhibitory effect of acenaphthenequinone bisulfite upon tumor growth in mice"The Biliography Information and Abstract of CA 49:61943 from Chemical Abstract CA Plus file (1955).

Trost et al., Generation and Alkylation of the Dianion (Homoenolate) of a 1–Indanone, *J. Org. Chem.*, Vol. 42, No. 19, 1977, pp. 3212–3214 (The Biliography Information), and Abstract of CA 87:151871 from Chemical Abstract CA Plus file (1977).

* cited by examiner-

C2-DISUBSTITUTED INDAN-1-OL COMPOUNDS, THEIR DERIVATIVES, PROCESSES FOR THEIR PREPARATION, AND THEIR USE AS PHARMACEUTICALS

FIELD OF THE INVENTION

The present invention relates to a C2-disubstituted indan-1-ol compound of formula (I), its compound derivatives and the pharmaceutically acceptable salt or physiologically functional derivative thereof.

BACKGROUND OF THE INVENTION

WO 98/55439 discloses derivatives of indan-1-ols for treating inflammations.

WO 97/20806 discloses 2-cyclopentanesulfanyl-, -sulfinyl- and -sulfonyl-substituted indan-1-ol derivatives having antiinflammatory action.

It is an object of the present invention to provide compounds which cause a reduction in weight in mammals and which are suitable for preventing and treating obesity.

SUMMARY OF THE INVENTION

The present invention relates to a C2-Disubstituted Indan-1-ol compound of formula I,

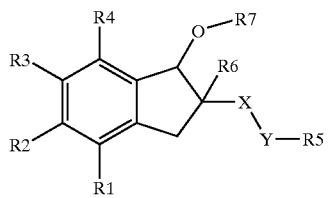

in which

A)
$R_1$, $R_2$, $R_3$, $R_4$ are each independently selected from the group consisting of H, F, Cl, Br, I, —CN; $N_3$, —$NO_2$, —OH, —O($C_1$–$C_8$)-alkyl, —O($C_3$–$C_8$)—cycloalkyl, —O—$CH_2$-phenyl, —O-phenyl, —O—CO—($C_1$–$C_8$)-alkyl, —O—CO—($C_3$–$C_8$)-cycloalkyl, —S(O)$_{0-2}$($C_1$–$C_8$)-alkyl, —S(O)$_{0-2}$($C_3$–$C_8$)-cycloalkyl, —$NH_2$, —NH—($C_1$–$C_8$)-alkyl, —NH—($C_3$–$C_8$)-cycloalkyl, —N[($C_1$–$C_8$)-alkyl]$_2$, —N[($C_3$–$C_8$)-cycloalkyl]$_2$, —NH—CO—($C_1$–$C_8$)-alkyl, —NH—CO—($C_3$–$C_8$)-cycloalkyl; —$SO_3H$, —$SO_2$—$NH_2$, —$SO_2$—NH—($C_1$–$C_8$)-alkyl, —$SO_2$—NH—($C_3$–$C_8$)-cycloalkyl, —NH—$SO_2$—$NH_2$, —NH—$SO_2$—($C_1$–$C_8$)-alkyl, —NH—$SO_2$—($C_3$–$C_8$)-cycloalkyl, —O—$CH_2$—COOH, —O—$CH_2$—CO—O($C_1$–$C_8$)-alkyl, —COOH, —CO—O($C_1$–$C_8$)-alkyl, —CO—O—($C_3$–$C_8$)-cycloalkyl, —CO—$NH_2$, —CO—NH($C_1$–$C_8$)-alkyl, —CO—N[($C_1$–$C_8$)-alkyl]$_2$, —($C_1$–$C_8$)-alkyl, —($C_3$–$C_8$)cycloalkyl, —($C_2$–$C_8$)-alkenyl, and —($C_2$–$C_8$)-alkynyl;
wherein the alkyl, alkenyl and alkynyl groups in each case one to seven hydrogen atoms which may be replaced by fluorine, or
one hydrogen may be replaced by —OH, —OC(O)$CH_3$, —O—$CH_2$-Ph, —$NH_2$, —NH—CO—$CH_3$, —N(COO$CH_2$Ph)$_2$,
an aryl radical wherein the aryl radical is phenyl, or 1- or 2-naphthyl; or a heterocycle wherein the heterocycle is 5-tetrazolyl, 1-[($C_1$–$C_6$)-alkyl]-5-tetrazolyl, 2-[($C_1$–$C_6$)-alkyl]-5-tetrazolyl, 1-imidazolyl, 1- or 4-[1,2,4]-triazolyl, 2- or 3-thienyl, 2- or 3-furyl, 2-, 3- or 4-pyridyl, 2-, 4- or 5-oxazolyl, 3-, 4- or 5-isoxazolyl, 2-, 4- or 5-thiazolyl, or 3-, 4- or 5-isothiazolyl;
wherein the aryl radical, or heterocycle may be substituted up to two times by F, Cl, Br, —CN, —OH, ($C_1$–$C_4$)-alkyl, —$CF_3$, —O—($C_1$–$C_4$)-alkyl, —S(O)$_{0-2}$($C_1$–$C_6$)-alkyl, —$NH_2$, —NH—$SO_2$—($C_1$–$C_4$)-alkyl, —COOH, —CO—O—($C_1$–$C_4$)-alkyl, or —CO—$NH_2$; and
wherein the alkyl groups one to seven hydrogen atoms which may be replaced by fluorine;
X is S, —SO, or —$SO_2$;
Y is —($CH_2$)$_p$, wherein p is 0–3;
$R_5$ is —$CF_3$, —($C_1$–$C_{18}$)-alkyl, or —($C_3$–$C_4$)-cycloalkyl and $C_6$–$C_8$)-cycloalkyl, wherein the alkyl groups one to seven hydrogen atoms which may be replaced by fluorine;
—($CH_2$)$_r$—$COR_{16}$, wherein r is 1–6 and $R_{16}$ may be —OH, —O—($C_1$–$C_6$)-alkyl or —$NH_2$;
—$CH_2$—CH(NH$R_{13}$)—$COR_8$, wherein $R_{13}$ may be H or —C(O)—($C_1$–$C_4$)-alkyl and $R_8$ may be —OH, —O—($C_1$–$C_6$)-alkyl or —$NH_2$;
Phenyl, 1- or 2-naphthyl, biphenyl or a heterocyclic radical, wherein the rings or ring systems of the phenyl, 1- or 2-naphthyl or heterocyclic radical may be substituted up to two times by F, Cl, Br, I, —CN, —OH, —O($C_1$–$C_8$)-alkyl, —O($C_3$–$C_8$)-cycloalkyl, —O—CO—($C_1$–$C_8$)-alkyl, —O—CO—($C_3$–$C_8$)-cycloalkyl, —S(O)$_{0-2}$($C_1$–$C_8$)-alkyl, —S(O)$_{0-2}$($C_3$–$C_8$)-cycloalkyl, —$NH_2$, —NH—($C_1$–$C_8$)-alkyl, —NH—($C_3$–$C_8$)-cycloalkyl, —N[($C_1$–$C_8$)-alkyl]$_2$, —N[($C_3$–$C_8$)-cycloalkyl]$_2$, —NH—CO—($C_2$–$C_8$)-alkyl, —NH—CO—($C_3$–$C_8$)-cycloalkyl; —$SO_3H$, —$SO_2$—$NH_2$, —$SO_2$—NH—($C_1$–$C_8$)-alkyl, —$SO_2$—NH—($C_3$–$C_8$)-cycloalkyl; —NH—$SO_2$—$NH_2$, —NH—$SO_2$—($C_1$–$C_8$)-alkyl, —NH—$SO_2$—($C_3$–$C_8$)-cycloalkyl, —O—$CH_2$—COOH, —O—$CH_2$—CO—O($C_1$–$C_8$)-alkyl, —COOH, —CO—O($C_1$–$C_8$)-alkyl, —CO—O—($C_3$–$C_8$)-cycloalkyl, —CO—$NH_2$, —CO—NH($C_1$–$C_8$)-alkyl, —CO—N[($C_1$–$C_8$)-alkyl]$_2$, —($C_1$–$C_8$)-alkyl, or —($C_3$–$C_8$)-cycloalkyl,
wherein the alkyl groups in each case one to seven hydrogen atoms may be replaced by fluorine;
$R_6$ is F, Cl, Br, —CN, —$CF_3$, —($C_1$–$C_{18}$)-alkyl, or —($C_3$–$C_8$)-cycloalkyl, wherein the alkyl groups one to seven hydrogen atoms may be replaced by fluorine;
—($CH_2$)$_s$—CH(NH$R_9$)—$COR_{10}$ wherein s is 1–6 and $R_9$ is H or —C(O)—($C_1$–$C_6$)-alkyl and wherein $R_{10}$ may be —OH, —O—($C_1$–$C_6$)-alkyl or —$NH_2$;
—($CH_2$)$_u$-aryl or —($CH_2$)$_u$-heteroaryl, wherein u is 0–6 and aryl may be phenyl, 1- or 2-naphthyl or biphenyl and the aryl or heteroaryl ring may be unsubstituted or substituted by at least one and up to two substituents such as
F, Cl, Br, I, —CN, —OH, —O($C_1$–$C_8$)-alkyl, or —O—CO—($C_1$–$C_8$)-alkyl, wherein the alkyl radicals one to seven hydrogen atoms may be replaced by fluorine;
—S(O)$_{0-2}$($C_1$–$C_8$)-alkyl, —$NH_2$, —NH—($C_1$–$C_8$)-alkyl, —NH—CO—($C_1$–$C_8$)-alkyl, —$SO_3H$, —$SO_2$—$NH_2$, —$SO_2$—NH—($C_1$–$C_8$)-alkyl, —NH—$SO_2$—($C_1$–$C_8$)- alkyl, —O—CH$_2$—COOH, —O—CH$_2$—CO—O(C$_1$–C$_8$)-alkyl, —COOH, —CO—O(C$_1$–C$_8$)-alkyl, —CO—NH$_2$, or —(C$_1$–C$_8$)-alkyl, wherein the alkyl groups one to seven hydrogen atoms may be replaced by fluorine; and R$_7$ is H; or

B)

R$_1$, R$_2$, R$_3$, R$_4$ are each independently selected from the group consisting of H, F, Cl, Br, I, —CN; N$_3$, —NO$_2$, —OH, —O(C$_1$–C$_8$)-alkyl, —O(C$_3$–C$_8$)-cycloalkyl, —O—CH$_2$-phenyl, —O-phenyl, —O—CO—(C$_1$–C$_8$)-alkyl, —O—CO—(C$_3$–C$_8$)-cycloalkyl, —S(O)$_{0-2}$(C$_1$–C$_8$)-alkyl, —S(O)$_{0-2}$(C$_1$–C$_8$)-cycloalkyl, —NH$_2$, —NH—(C$_1$–C$_8$)-alkyl, —H—(C$_3$–C$_8$)-cycloalkyl N[(C$_1$–C$_8$)-alkyl]$_2$, —N[(C$_3$–C$_8$)-cycloalkyl]$_2$, —NH—CO—(C$_1$–C$_8$)-alkyl, —NH—CO—(C$_3$–C$_8$)-cycloalkyl; —SO$_3$H, —SO$_2$—NH$_2$, —SO$_2$—NH—(C$_1$–C$_8$)-alkyl, —SO$_2$—NH—(C$_3$–C$_8$)-cycloalkyl, —NH—SO$_2$—NH$_2$, —NH—SO$_2$—(C$_1$–C$_8$)-alkyl, —NH—SO$_2$—(C$_3$–C$_8$)-cycloalkyl, —O—CH$_2$—COOH, —O—CH$_2$—CO—O(C$_1$–C$_8$)-alkyl, —COOH, —CO—O(C$_1$–C$_8$)-alkyl, —CO—O—(C$_3$–C$_8$)-cycloalkyl, —CO—NH$_2$, —CO—NH (C$_1$–C$_8$)-alkyl, —CO—N[(C$_1$–C$_8$)-alkyl]$_2$, —(C$_1$–C$_8$)-alkyl, —(C$_3$–C$_8$)cycloalkyl, —(C$_2$–C$_8$)-alkenyl, and —(C$_2$–C$_8$)-alkynyl;

wherein the alkyl, alkenyl and alkynyl groups in each case one to seven hydrogen atoms may be replaced by fluorine; or one hydrogen may be replaced by —OH, —OC(O)CH$_3$, —O—CH$_2$-Ph, —NH$_2$, —NH—CO—CH$_3$, —N(COOCH$_2$Ph)$_2$;

an aryl radical wherein the aryl radical is phenyl, 1- or 2-naphthyl; or a heterocycle wherein the heterocycle is 5-tetrazolyl, 1-[(C$_1$–C$_6$)-alkyl]-5-tetrazolyl, 2-[(C$_1$–C$_6$)-alkyl]-5-tetrazolyl, 1-imidazolyl, 1- or 4-[1,2,4]-triazolyl, 2- or 3-thienyl, 2- or 3-furyl, 2-, 3- or 4-pyridyl, 2-, 4- or 5-oxazolyl, 3-, 4- or 5-isoxazolyl, 2-, 4- or 5-thiazolyl, or 3-, 4- or 5-isothiazolyl, wherein the aryl radical or heterocycle may be substituted up to two times by F, Cl, Br, —CN, —OH, —(C$_1$–C$_4$)-alkyl, —CF$_3$, —O—(C$_1$–C$_4$)-alkyl, —S(O)$_{0-2}$(C$_1$–C$_6$)-alkyl, —NH$_2$, —NH—SO$_2$—(C$_1$–C$_4$)-alkyl, —COOH, —CO—O—(C$_1$–C$_4$)-alkyl, or —CO—NH$_2$, and wherein the alkyl groups one to seven hydrogen atoms may be replaced by fluorine;

X is S, —SO, or —SO$_2$;

Y is —(CH$_2$)$_p$, where p is 0–3;

R$_5$ is —CF$_3$, —(C$_1$–C$_{18}$)-alkyl, —(C$_3$–C$_4$)-cycloalkyl, or —(C$_6$–C$_8$)-cycloalkyl, wherein the alkyl groups one to seven hydrogen atoms may be replaced by fluorine;

—(CH$_2$)$_r$—COR$_{16}$, wherein r is 1–6 and R$_{16}$ may be —OH, —O—(C$_1$–C$_6$)-alkyl or —NH$_2$;

—CH$_2$—CH(NHR$_{13}$)—COR$_8$, wherein R$_{13}$ may be H or —C(O)—(C$_1$–C$_4$)-alkyl and R$_8$ may be —OH, —O—(C$_1$–C$_6$)-alkyl or —NH$_2$;

Phenyl, 1- or 2-naphthyl, biphenyl or a heterocyclic radical, wherein the rings or ring systems of the phenyl, 1- or 2-naphthyl or heterocyclic radical may be substituted up to two times by F, Cl, Br, I, —CN, —OH, —O(C$_1$–C$_8$)-alkyl, —O(C$_3$–C$_8$)-cycloalkyl, —O—CO—(C$_1$–C$_8$)-alkyl, —O—CO—(C$_3$–C$_8$)-cycloalkyl, —S(O)$_{0-2}$(C$_1$–C$_8$)-alkyl, —S(O)$_{0-2}$(C$_3$–C$_8$)-cycloalkyl, —NH$_2$, —NH—(C$_1$–C$_8$)-alkyl, —NH—(C$_3$–C$_8$)-cycloalkyl, —N[(C$_1$–C$_8$)-alkyl]$_2$, —N[(C$_3$–C$_8$)-cycloalkyl]$_2$, —NH—CO—(C$_2$–C$_8$)-alkyl, —NH—CO—(C$_3$–C$_8$)-cycloalkyl; —SO$_3$H, —SO$_2$—NH$_2$, —SO$_2$—NH—(C$_1$–C$_8$)-alkyl, —SO$_2$—NH—(C$_3$–C$_8$)-cycloalkyl; —NH—SO$_2$—NH$_2$, —NH—SO$_2$—(C$_1$–C$_8$)-alkyl, —NH—SO$_2$—(C$_3$–C$_8$)-cycloalkyl, —O—CH$_2$—COOH, —O—CH$_2$—CO—O(C$_1$–C$_8$)-alkyl, —COOH, —CO—O(C$_1$–C$_8$)-alkyl, —CO—O—(C$_3$–C$_8$)-cycloalkyl, —CO—NH$_2$, —CO—NH(C$_1$–C$_8$)-alkyl, —CO—N[(C$_1$–C$_8$)-alkyl]$_2$, —(C$_1$–C$_8$)-alkyl, or —(C$_3$–C$_8$)-cycloalkyl, wherein the alkyl groups in each case one to seven hydrogen atoms may be replaced by fluorine;

R$_6$ is F, Cl, Br, —CN, —CF$_3$, —(C$_1$–C$_{18}$)-alkyl, or —(C$_3$–C$_8$)-cycloalkyl, wherein the alkyl groups one to seven hydrogen atoms may be replaced by fluorine;

—(CH$_2$)$_t$—COR$_8$, where t is 0–6 and R$_8$ may be —OH, —O—(C$_1$–C$_6$)-alkyl or —NH$_2$; —(CH$_2$)$_s$—CH(NHR$_9$)—COR$_{10}$ wherein s is 1–6 and R$_9$ may be H or —C(O)—(C$_1$–C$_6$)-alkyl and R$_{10}$ may be —OH, —O—(C$_1$–C$_6$)-alkyl or —NH$_2$;

—(CH$_2$)$_u$—aryl or —(CH$_2$)$_u$-heteroaryl, where u is 0–6 and aryl may be phenyl, 1- or 2-naphthyl or biphenyl and the aryl or heteroaryl ring may be unsubstituted or substituted by at least one and up to two substituents such as F, Cl, Br, I, —CN, —OH, —O(C$_1$–C$_8$)-alkyl, or —O—CO—(C$_1$–C$_8$)-alkyl, wherein the alkyl radicals one to seven hydrogen atoms may be replaced by fluorine;

—S(O)$_{0-2}$(C$_1$–C$_8$)-alkyl, —NH$_2$, —NH—(C$_1$–C$_8$)-alkyl, —NH—CO—(C$_1$–C$_8$)-alkyl, —SO$_3$H, —SO$_2$—NH$_2$, —SO$_2$—NH—(C$_1$–C$_8$)-alkyl, —NH—SO$_2$—(C$_1$–C$_8$)-alkyl, —O—CH$_2$—COOH, —O—CH$_2$—CO—O(C$_1$–C$_8$)-alkyl, —COOH, —CO—O(C$_1$–C$_8$)-alkyl, —CO—NH$_2$, or —(C$_1$–C$_8$)-alkyl, wherein the alkyl groups in each case one to seven hydrogen atoms may be replaced by fluorine;

R$_7$ is —(C$_1$–C$_{12}$)-alkyl, —(C$_3$–C$_8$)-cycloalkyl, wherein the alkyl radicals one to seven hydrogen atoms may be replaced by fluorine;

—CO—O(C$_1$–C$_6$)-alkyl, —CO—O(C$_3$–C$_8$)-cycloalkyl, —C(O)—(C$_1$–C$_8$)-alkyl, —C(O)—(C$_3$–C$_8$)-cycloalkyl, —C(O)-phenyl, —C(O)—CH(NHR$_{12}$)—(C$_1$–C$_8$)-alkyl, phenyl, 1- or 2-naphthyl, biphenyl, 2-, 3- or 4-pyridyl, wherein the phenyl, 1- or 2-naphthyl, biphenyl, 2-, 3- or 4-pyridyl may be substituted up to two times by F, Cl, Br, —CN, —OH, —(C$_1$–C$_4$)-alkyl, —CF$_3$, —O—(C$_1$–C$_4$)-alkyl, —S(O)$_{0-2}$(C$_1$–C$_6$)-alkyl, —NH$_2$, —NH—SO$_2$-(C$_1$–C$_4$)-alkyl, —CH$_2$—COOH, —O—CH$_2$—CO—O(C$_1$–C$_8$)-alkyl, —COOH, —CO—O—(C$_1$–C$_4$)-alkyl, —CO—NH$_2$;

—(CH$_2$)—R$_{10}$; or

—(CH$_2$)$_s$—R$_{11}$, wherein s is 2 or 3;

R$_{10}$ is —(C$_1$–C$_{12}$)-alkyl, or —(C$_3$–C$_8$)-cycloalkyl, wherein the alkyl radicals one to seven hydrogen atoms may be replaced by fluorine;

—COOH, —CONH$_2$, —CO—O(C$_1$–C$_6$)-alkyl, —CO—O(C$_3$–C$_8$)-cycloalkyl;

phenyl, 1- or 2-naphthyl, biphenyl, 2-, 3- or 4-pyridyl, 2- or 3-furyl or 2- or 3-thienyl, wherein the phenyl, 1- or 2-naphthyl, biphenyl, 2-, 3- or 4-pyridyl, 2- or 3-furyl or 2- or 3-thienyl may be substituted up to two times by F, Cl, Br, —CN, —OH, —($C_1$–$C_4$)-alkyl, —$CF_3$, —O—($C_1$–$C_4$)-alkyl, —S(O)$_{0-2}$($C_1$–$C_6$)-alkyl, —$NH_2$, —NH—$SO_2$—($C_1$–$C_4$)-alkyl, —O—$CH_2$—COOH, —O—$CH_2$—CO—O($C_1$–$C_8$)-alkyl, —COOH, —CO—O—($C_1$–$C_4$)-alkyl, or —CO—$NH_2$;

$R_{11}$ is —($C_1$–$C_{12}$)-alkyl, —($C_3$–$C_8$)-cycloalkyl, wherein the alkyl radicals one to seven hydrogen atoms may be replaced by fluorine;

—COOH, —$CONH_2$, —CO—O($C_1$–$C_6$)-alkyl, —CO—O($C_3$–$C_8$)-cycloalkyl;

phenyl, 1- or 2-naphthyl, biphenyl, 2-, 3- or 4-pyridyl, 2- or 3-furyl or 2- or 3-thienyl or 1-imidazolyl, wherein the phenyl, 1- or 2-naphthyl, biphenyl, 2-, 3- or 4-pyridyl, 2- or 3-furyl or 2- or 3-thienyl or 1-imidazolyl may be substituted up to two times by F, Cl, Br, —CN, —OH, —($C_1$–$C_4$)-alkyl, —$CF_3$, —O—($C_1$–$C_4$)-alkyl, —S(O)$_{0-2}$($C_1$–$C_6$)-alkyl, —$NH_2$, —NH—$SO_2$—($C_1$–$C_4$)-alkyl, —O—$CH_2$—COOH, —O—$CH_2$—CO—O($C_1$–$C_8$)-alkyl, —COOH, —CO—O—($C_1$–$C_4$)-alkyl, or —CO—$NH_2$;

$R_{12}$ is H, or —C(O)—($C_1$–$C_6$)-alkyl; or a pharmaceutically acceptable salt or physiologically functional derivative thereof.

The invention furthermore provides a process for preparing the compounds of the formula I which comprises obtaining the compounds of the formula I by proceeding according to the reaction scheme below (see Table A).

DETAILED DESCRIPTION OF THE INVENTION

Definition of Terms

As used above, and throughout the description of the invention, the following terms, unless otherwise indicated, shall be understood to have the following meanings.

All references to "compound(s) according to formula I" in the following text relate to compound(s) of the formula I as described above and their racemates, racemic mixtures, pure enantiomers, diastereomers and their mixtures thereof.

"Alkyl", "alkenyl" and "alkynyl" radicals in the substituents $R_1$, $R_2$, $R_3$, $R_4$, $R_5$, $R_6$, $R_7$, $R_8$, $R_9$, $R_{10}$, $R_{11}$ and $R_{12}$ can be straight-chain or branched.

"Heterocycle" or "heterocyclic radical" is to be understood as meaning ring systems which, in addition to carbon, also contain heteroatoms, such as, for example, nitrogen, oxygen or sulfur. This definition furthermore includes ring systems in which the heterocycle or heterocyclic radical is fused with benzene rings. Preferred heterocycles or heterocyclic radicals are:

heteroaryls, such as
benzimidazolyl,
1-[($C_1$–$C_6$)-alkyl]benzimidazolyl,
imidazolyl,
2- or 3-thienyl,
2- or 3-furyl,
benzoxazolyl,
benzothiazolyl,
2-, 3- or 4-pyridyl,
pyrimidinyl,
4-, 5- or 6-pyridazin-2H-yl-3-one,
4-, 5- or 6-pyridazin-2-($C_1$–$C_8$)-alkyl-2H-yl-3-one,
2-benzyl-4-, -5- or -6-pyridazin-2H-yl-3-one,
3- or 4-pyridazinyl,
2-, 3-, 4- or 8-quinolinyl,
1-, 3- or 4-isoquinolinyl,
1-phthalazinyl,
3- or 4-cinnolinyl,
2- or 4-quinazolinyl,
2-pyrazinyl,
2-quinoxalinyl,
2-, 4- or 5-oxazolyl,
3-, 4- or 5-isoxazolyl,
2-, 4- or 5-thiazolyl,
3-, 4- or 5-isothiazolyl,
1-[($C_1$–$C_6$)-alkyl]-2-, -4- or -5-imidazolyl,
3-, 4- or 5-pyrazolyl,
1-[($C_1$–$C_6$)-alkyl]-3-, -4- or -5-pyrazolyl,
1- or 4-[1,2,4]-triazolyl,
4- or 5-[1,2,3]-triazolyl,
1-[($C_1$–$C_6$)-alkyl]-4- or -5-[1,2,3]triazolyl,
3-, 4- or 7-indolyl,
N-[($C_1$–$C_6$)-alkyl]-3-, -4- or -7-indolyl
2-[($C_1$–$C_6$)-alkyl]-3(2H)-indazolyl,
1-[($C_1$–$C_6$)-alkyl]-3(1H)-indazolyl,
5-tetrazolyl,
1-[($C_1$–$C_6$)-alkyl]-1H-tetrazolyl,
2-[($C_1$–$C_6$)-alkyl]-2H-tetrazolyl.

"Pharmaceutically acceptable salt", which may also be termed "physiologically acceptable salts", is particularly suitable for medical applications, due to its greater solubility in water compared with the initial compound. The salt must have a pharmaceutically acceptable anion or cation. A suitable pharmaceutically acceptable salt as an acid addition salt of a compound of the invention, for example, is a salt of an inorganic acid such as hydrochloric acid, hydrobromic, phosphoric, metaphosphoric, nitric, or sulfuric acid, or of organic acids such as, for example, acetic, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric, trifluoroacetic, L-ascorbic, salicylic acid, 1,2-benzisothiazol-3(2H)-one, or 6-methyl-1,2,3-oxathiazin-4(3H)-one 2,2-dioxide. For medicinal purposes, particular preference is given to using the chlorine salt. A suitable pharmaceutically acceptable salt as a base addition salt of a compound of the invention, for example, is an ammonium, alkali metal (such as sodium and potassium) and alkaline earth metal (such as magnesium and calcium) salt.

A salt with a pharmaceutically unacceptable anion likewise is included within the scope of the present invention as useful intermediates for preparing or purifying a pharmaceutically acceptable salt or for use in nontherapeutic applications, for example in-vitro, applications.

"Patient" means a mammal including a human.

"Physiologically functional derivative" means any physiologically tolerated derivative of a compound of the invention, e.g. a prodrug such as an ester that is able on administration to a patient, to form (directly or indirectly) such a compound or an active metabolite thereof.

A prodrug of the compounds according to the invention are another aspect of this invention. Such prodrugs can be metabolized in vivo to give a compound according to the invention and include, for example glucuronides, sulfuric acid esters, glycosides and ribosides. These prodrugs may or may not be active themselves.

The compounds of the formula I may also be present in various polymorphous forms, for example as amorphous and crystalline polymorphous forms. All polymorphous forms of the compounds of the formula I are included within the scope of the invention and are another aspect of the invention.

All references to "compound(s) according to formula (I)" in the following text relate to compound(s) of the formula (I) as described above and their salts, solvates and physiologically functional derivatives as described herein.

Embodiments

A particular embodiment of the invention is the compound of formula (I) wherein:

$R_1$, $R_2$, $R_3$, $R_4$ are each independently selected from the group consisting of H, F, Cl, Br, I, —CN; $N_3$, —$NO_2$, —OH, —O($C_1$–$C_8$)-alkyl, —O($C_3$–$C_8$)-cycloalkyl, —O—$CH_2$-phenyl, —O-phenyl, —O—CO—($C_1$–$C_8$)-alkyl, —O—CO—($C_3$–$C_8$)-cycloalkyl, —S(O)$_{0-2}$($C_1$–$C_8$)-alkyl, —S(O)$_{0-2}$($C_3$–$C_8$)-cycloalkyl, —$NH_2$, —NH—($C_1$–$C_8$)-alkyl, —NH—($C_3$–$C_8$)-cycloalkyl, —N[($C_1$–$C_8$)-alkyl]$_2$, —N[($C_3$–$C_8$)-cycloalkyl]$_2$, —NH—CO—($C_1$–$C_8$)-alkyl, —NH—CO—($C_3$–$C_8$)-cycloalkyl; —$SO_3$H, —$SO_2$—$NH_2$, —$SO_2$—NH—($C_1$–$C_8$)-alkyl, —$SO_2$—NH—($C_3$–$C_8$)-cycloalkyl, —NH—$SO_2$—$NH_2$, —NH—$SO_2$—($C_1$–$C_8$)-alkyl, —NH—$SO_2$—($C_3$–$C_8$)-cycloalkyl, —O—$CH_2$—COOH, —O—$CH_2$—CO—O($C_1$–$C_8$)-alkyl, —COOH, —CO—O($C_1$–$C_8$)-alkyl, —CO—O—($C_3$–$C_8$)-cycloalkyl, —CO—$NH_2$, —CO—NH($C_1$–$C_8$)-alkyl, —CO—N[($C_1$–$C_8$)-alkyl]$_2$, —($C_1$–$C_8$)-alkyl, —($C_3$–$C_8$)cycloalkyl, —($C_2$–$C_8$)-alkenyl, and —($C_2$–$C_8$)-alkynyl;

wherein the alkyl, alkenyl and alkynyl groups in each case one to seven hydrogen atoms which may be replaced by fluorine, or one hydrogen may be replaced by —OH, —OC(O)$CH_3$, —O—$CH_2$-Ph, —$NH_2$, —NH—CO—$CH_3$, —N(COOCH$_2$Ph)$_2$;

an aryl radical wherein the aryl radical is phenyl, or 1- or 2-naphthyl; or a heterocycle wherein the heterocycle is 5-tetrazolyl, 1-[($C_1$–$C_6$)-alkyl]-5-tetrazolyl,
2-[($C_1$–$C_6$)-alkyl]-5-tetrazolyl,
1-imidazolyl,
1- or 4-[1,2,4]-triazolyl,
2- or 3-thienyl,
2- or 3-furyl,
2-, 3- or 4-pyridyl,
2-, 4- or 5-oxazolyl,
3-, 4- or 5-isoxazolyl,
2-, 4- or 5-thiazolyl, or
3-, 4- or 5-isothiazolyl;

wherein the aryl radical or heterocycle may be substituted up to two times by F, Cl, Br, —CN, —OH, ($C_1$–$C_4$)-alkyl, —$CF_3$, —O—($C_1$–$C_4$)-alkyl, —S(O)$_{0-2}$($C_1$–$C_6$)-alkyl, —$NH_2$, —NH—$SO_2$—($C_1$–$C_4$)-alkyl, —COOH, —CO—O—($C_1$–$C_4$)-alkyl, or —CO—$NH_2$; and wherein the alkyl groups one to seven hydrogen atoms which may be replaced by fluorine;

X is S, —SO, or —$SO_2$;

Y is —(CH$_2$)$_p$, wherein p is 0–3;

$R_5$ is —$CF_3$, —($C_1$–$C_{18}$)-alkyl, or —($C_3$–$C_4$)-cycloalkyl and —($C_6$–$C_8$)-cycloalkyl, wherein the alkyl groups one to seven hydrogen atoms which may be replaced by fluorine;

—(CH$_2$)$_r$—COR$_{16}$, wherein r is 1–6 and $R_{16}$ may be —OH, —O—($C_1$–$C_6$)-alkyl or —$NH_2$;

—$CH_2$—CH(NHR$_{13}$)—COR$_8$, wherein $R_{13}$ may be H or —C(O)—($C_1$–$C_4$)-alkyl and $R_8$ may be —OH, —O—($C_1$–$C_6$)-alkyl or —$NH_2$;

Phenyl, 1- or 2-naphthyl, biphenyl or a heterocyclic radical, wherein the rings or ring systems of the phenyl, or 1- or 2-naphthyl or heterocyclic radical may be substituted up to two times by F, Cl, Br, I, —CN, —OH, —O($C_1$–$C_8$)-alkyl, —O($C_3$–$C_8$)-cycloalkyl, —O—CO—($C_1$–$C_8$)-alkyl, —O—CO—($C_3$–$C_8$)-cycloalkyl, —S(O)$_{0-2}$($C_1$–$C_8$)-alkyl, —S(O)$_{0-2}$($C_3$–$C_8$)-cycloalkyl, —$NH_2$, —NH—($C_1$–$C_8$)-alkyl, —NH—($C_3$–$C_8$)-cycloalkyl, —N[($C_1$–$C_8$)-alkyl]$_2$, —N[($C_3$–$C_8$)-cycloalkyl]$_2$, —NH—CO—($C_2$–$C_8$)-alkyl, —NH—CO—($C_3$–$C_8$)-cycloalkyl; —$SO_3$H, —$SO_2$—$NH_2$, —$SO_2$—NH—($C_1$–$C_8$)-alkyl, —$SO_2$—NH—($C_3$–$C_8$)-cycloalkyl; —NH—$SO_2$—$NH_2$, —NH—$SO_2$—($C_1$–$C_8$)-alkyl, —NH—$SO_2$—($C_3$–$C_8$)-cycloalkyl, —O—$CH_2$—COOH, —O—$CH_2$—CO—O($C_1$–$C_8$)-alkyl, —COOH, —CO—O($C_1$–$C_8$)-alkyl, —CO—O—($C_3$–$C_8$)-cycloalkyl, —CO—$NH_2$, —CO—NH($C_1$–$C_8$)-alkyl, —CO—N[($C_1$–$C_8$)-alkyl]$_2$, —($C_1$–$C_8$)-alkyl, or —($C_3$–$C_8$)-cycloalkyl, wherein the alkyl groups in each case one to seven hydrogen atoms may be replaced by fluorine;

$R_6$ is F, Cl, Br, or —($C_1$–$C_{18}$)-alkyl, wherein the alkyl groups one to seven hydrogen atoms may be replaced by fluorine; and $R_7$ is H; or a pharmaceutically acceptable salt or physiologically functional derivative thereof.

Another particular embodiment of the invention is the compound of formula (I) wherein:

$R_1$, $R_2$, $R_3$, $R_4$ are each independently selected from the group consisting of H, F, Cl, Br, and —($C_1$–$C_8$)-alkyl, wherein the alkyl groups in each case one to seven hydrogen atoms which may be replaced by fluorine;

phenyl, wherein phenyl may be substituted up to two times by F, Cl, Br, —OH, —O($C_1$–$C_4$)-alkyl, or —($C_1$–$C_4$)-alkyl, wherein the alkyl groups one to seven hydrogen atoms which may be replaced by fluorine;

X is S, or —$SO_2$;

Y is —(CH$_2$)$_p$, wherein p is 0–1;

$R_5$ is —$CF_3$, —($C_1$–$C_{18}$)-alkyl, or —($C_3$–$C_4$ and $C_6$–$C_8$)-cycloalkyl, wherein the alkyl groups one to seven hydrogen atoms which may be replaced by fluorine;

Phenyl, wherein phenyl may be substituted up to two times by F, Cl, Br, —OH, —O($C_1$–$C_8$)-alkyl, or —($C_1$–$C_8$)-alkyl, wherein the alkyl groups in each case one to seven hydrogen atoms may be replaced by fluorine;

$R_6$ is F, Cl, Br, or —($C_1$–$C_{18}$)-alkyl, wherein the alkyl groups one to seven hydrogen atoms may be replaced by fluorine;

$R_7$ is H; or a pharmaceutically acceptable salt or physiologically functional derivative thereof.

Another particular embodiment of the invention provides a process for preparing the compounds of the formula I which comprises obtaining the compounds of the formula I by proceeding according to the reaction scheme below (see Table A):

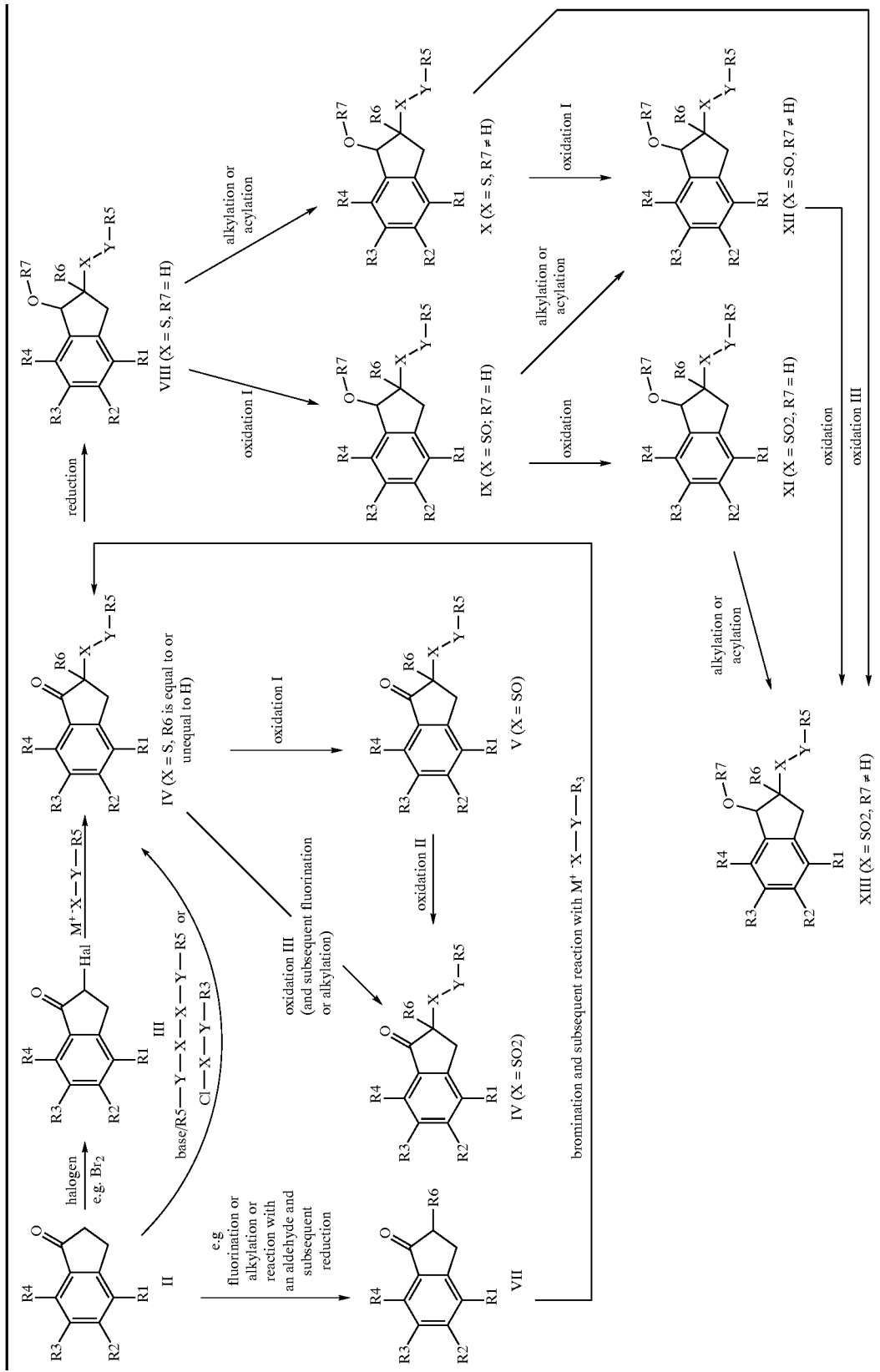

To this end, compounds of the formula II,

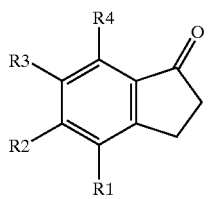

Formula II in which $R_1$, $R_2$, $R_3$ and $R_4$ are as defined above are converted with a halogen, such as, for example, bromine or chlorine, into a compound of the formula III.

The compounds of the formula III are converted further with metal salts of thiols of the formula H—X—Y—$R_5$, where X is sulfur and Y and $R_5$ are as defined above into compounds of the formula IV where X=S and $R_6$=H. These metal salts can be employed as such or they can be generated in solution in situ from the thiol and a base, such as, for example, aqueous sodium hydroxide.

On the other hand, compounds of the formula IV where X=S and $R_6$=H can be obtained by reacting compounds of the formula II with a base, such as, for example, lithium diisopropylamide, for example in tetrahydrofuran, and with a disulfide of the formula $R_5$—Y—X—X—Y—$R_5$ in which $R_5$ and Y are as defined above and X=S; alternatively, instead of the disulfide, it is also possible to use a sulfenyl chloride of the formula Cl—X—Y—$R_5$ where X=S and Y and $R_5$ are as defined above (see, for example, D. Seebach et al.; Chem. Ber. 109, 1601–1616 (1976)).

Compounds of the formula IV in which X=S and $R_6$ is not hydrogen can be obtained, for example, as follows: compounds of the formula II are subjected, for example, to a fluorination, alkylation or a condensation with an aldehyde and subsequent reduction, giving compounds of the formula VII which for their part can be converted, for example, after bromination with compounds of the formula $M^{+-}$X—Y—$R_5$ where X=S and Y and $R_5$ have the meanings described above to give compounds of the formula IV where X=S and $R_6$ is not hydrogen.

Compounds of the formula V in which X=SO and $R_6$ is not hydrogen can be prepared, for example, by selective oxidation of the compound of the formula IV in which X=S, using one equivalent of peroxytrifluoroacetic acid (C. G. Venier et al.; J. Org. Chem. 47, 3773 (1982)). The preparation of the sulfoxides from the sulfides can also be carried out using manganese dioxide or chromic acid (D. Edwards et al.; J. Chem. Soc. 1954, 3272). Furthermore suitable for this oxidation is hydrogen peroxide in acetic anhydride (A. V. Sviridova et al.; J. Org. Chem (Russ), English Transl.; 7, 2577 (1971)).

Compounds of the formula VI in which X=$SO_2$ and $R_6$ is not hydrogen can be obtained by oxidation using, for example, $2KHSO_5 \times KHSO_4 \times K_2SO_4$ (Oxone), either from compounds of the formula IV in which X=S and $R_6$ is not hydrogen or from compounds of the formula V in which X=SO and $R_6$ is not hydrogen (see, for example, M. Hudlicky, Oxidations in Organic Chemistry, ACS Monograph 186, American Chemical Society, Washington, D.C., 1990).

Compounds of the formula V, VI or VII in which X=S, SO or $SO_2$ and $R_6$ is not hydrogen, for example phenyl, and Y is a bond and $R_5$ has the meaning described above can also be obtained by reacting compounds of the formula V in which X=S and $R_6$=H and Y is a bond and $R_5$=phenyl with diphenyliodonium chloride, for example. The resulting compounds can either be converted stepwise into the corresponding compounds in which X=SO or $SO_2$; or they are subsequently disulfurized with zinc/acetic acid and are then available for further reactions according to the scheme above.

Compounds of the formula XIV and XV in which X=SO or $SO_2$, $R_6$=H and Y=a bond (=$(CH_2)_m$ where m=0) can also, alternatively, be prepared according to the scheme below (shown for the preparation of the aryl sulfoxides (H. J. Monteiro et al.; Tetrahedron Letters 11, 921–924 (1975) and aryl sulfones (A. K. Maiti et al.; Tetrahedron 50, 10483–10490 (1994)):

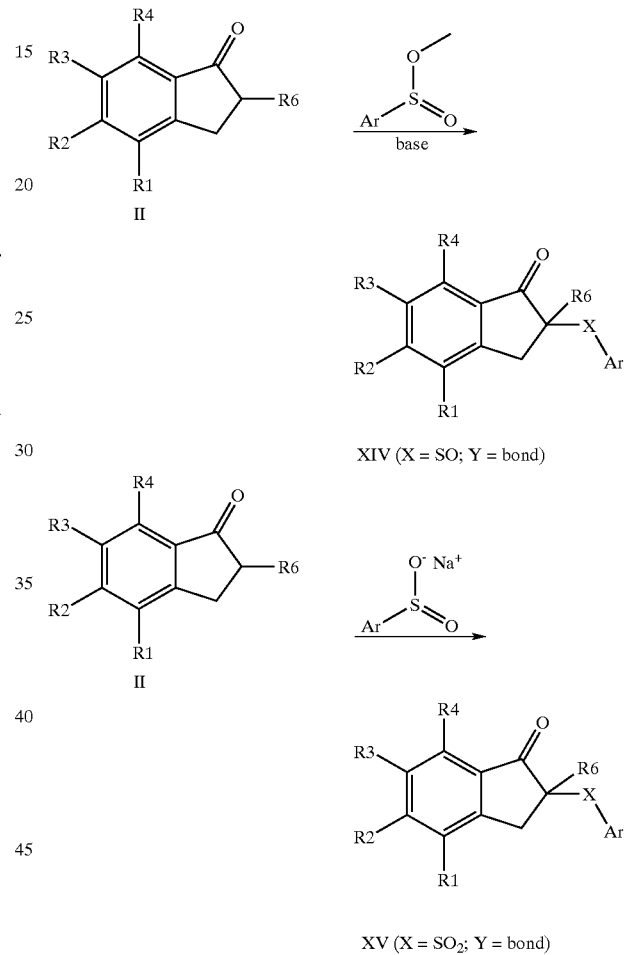

Compounds of the formula VI in which X=$SO_2$ and $R_6$ is not hydrogen and Y and $R_5$ have the meanings described above can also be obtained by subjecting compounds of the formula VI in which X=$SO_2$ and $R_6$=H and Y and $R_5$ are as described above to a fluorination or alkylation, for example.

Compounds of the formula VII in which X=S and $R_6$ is H or is not H can be obtained by reducing compounds of the formula IV in which X=S and $R_6$ is H or is not H. Oxidation of the compounds of the formula VIII gives compounds of the formula IX or XI in which X=SO or $SO_2$. Alkylation or acylation of compounds of the formula XI in which X=$SO_2$ and $R_7$=H gives access to compounds of the formula XII in which X=$SO_2$ and $R_7$ is not H. Compounds of the formula X in which X=S and $R_7$ is not H can be prepared by alkylating or acylating compounds of the formula VIII in which X=S and $R_7$=H. Compounds of the formula XII in which X=SO and $R_7$ is not H can be prepared either by oxidation from compounds of the formula X or by alkylation or acylation of compounds of the formula IX.

Inorganic acids suitable for forming salts are, for example: hydrohalic acids, such as hydrochloric acid and hydrobromic acid, and also sulfuric acid, phosphoric acid and amidosulfonic acid.

Organic acids suitable for salt formation which may be mentioned are, for example: formic acid, acetic acic, benzoic acid, p-toluenesulfonic acid, benzenesulfonic acid, succinic acid, fumaric acid, maleic acid, lactic acid, tartaric acid, citric acid, L-ascorbic acid, salicylic acid, isethionic acid, methanesulfonic acid, trifluoromethanesulfonic acid, 1,2-benzisothiazol-3(2H)-one, 6-methyl-1,2,3-oxathiazin-4(3H)-one 2,2-dioxide.

Another particular embodiment of the invention the present compounds are administered in combination with insulin.

Another particular embodiment of the invention, the compounds of the invention are administered in combination with a sulfonylurea such as, for example, tolbutamide, glibenclamide, glimepiride, glipizide, gliquidone, glisoxepide, glibornuride or gliclazide.

Another particular embodiment of the invention, the compounds of the present invention are administered in combination with a biguanide such as, for example, metformin.

Another particular embodiment of the invention, the compounds of the present invention are administered in combination with a meglitinide such as, for example, repaglinide.

Another particular embodiment of the invention, the compounds of the present invention are administered in combination with a thiazolidinedione such as, for example, troglitazone, ciglitazone, pioglitazone, rosiglitazone or the compounds disclosed by Dr. Reddy's Research Foundation in WO 97/41097, in particular 5-[[4-[(3,4-dihydro-3-methyl-4-oxo-2-quinazolinylmethoxy]phenyl]methyl]-2,4-thiazolidinedione.

Another particular embodiment of the invention, the compounds of the present invention are administered in combination with a monoamine oxidase inhibitor such as disclosed, for example, in WO 01/12176. Particularly suitable for this purpose are [3(S),3a(S)]-3-methoxymethyl-7-[4,4,4-trifluorobutoxy]-3,3a,4,5-tetrahydro-1H-oxazolo[3,4-a]quinolin-1-one, (R)-5-(methoxymethyl)-3-[6-(4,4,4-trifluorobutoxy)benzofuran-3-yl]oxazolidin-2-one or (R)-5-(methoxymethyl)-3-[6-cyclopropylmethoxybenzofuran-3-yl]oxazolidin-2-one.

Another particular embodiment of the invention, the compounds of the present invention are administered in combination with an α-glucosidase inhibitor such as, for example, miglitol or acarbose.

Another particular embodiment, the present compounds are administered in combination with an hCNTF (human ciliary neurotrophic factor) or derivatives thereof, such as, for example, $CNTF_{AX15}$ or modified $CNTF_{AX15}$, such as disclosed, for example, in Lambert et al., PNAS 98, 4652–4657.

Another particular embodiment of the invention, the compounds of the present invention are administered in combination with an active compound which acts on the ATP-dependent potassium channel of the beta cells, such as, for example, tolbutamide, glibenclamide, glimepiride, glipizide, gliclazide or repaglinide.

Another particular embodiment of the invention, the compounds of the present invention are administered in combination with an antihyperlipidemic active compound or an antilipidemic active compound such as, for example, cholestyramine, colestipol, clofibrate, gemfibrozil, lovastatin, pravastatin, simvastatin, atorvastatin, cerivastatin, fluvastatin, probucol, ezetimibe or dextrothyroxine.

Another particular embodiment of the invention, the compounds of the present invention are administered in combination with more than one of the aforementioned compounds, for example in combination with a sulfonylurea and metformin, a sulfonylurea and acarbose, repaglinide and metformin, insulin and a sulfonylurea, insulin and metformin, insulin and troglitazone, insulin and lovastatin, etc.

Another further particular embodiment of the invention is where the compound of formula (I) may be administered in combination with one or more antiadipose agents or appetite-controlling active compounds. Such active compounds may be selected from the group consisting of for example, from CART agonists, NPY antagonists, melanocortin 3 or 4 (MC3 or MC4) agonists, melanin-concentrating hormone (MCH) antagonists, orexin antagonists, H3 agonists, TNF agonists, CRF agonists, CRF BP antagonists, urocortin agonists, β3 adrenoceptor agonists, CCK agonists, serotonin re-uptake inhibitors, mixed serotonin and noradrenalin reuptake inhibitors, 5HT modulators, bombesin agonists, galanin antagonists, glucocorticoid receptor modulators, growth hormone, growth-hormone-releasing compounds, TRH agonists, uncoupling protein 2 or 3 modulators, leptin receptor agonists, leptin mimetics, dopamine agonists (bromocriptine, doprexin), lipase/amylase inhibitors, cannabinoid receptor 1 antagonists, modulators of acylation-stimulating protein (ASP), PPAR modulators, RXR modulators or TR-β agonists.

Another particular embodiment of the invention, the antiadipose agent is leptin or modified leptin.

Another particular embodiment, the antiadipose agent is dexamphetamine or amphetamine.

Another particular embodiment, the antiadipose agent is fenfluramine or dexfenfluramine.

Another particular embodiment, the antiadipose agent is sibutramine or the mono- and bis-demethylated active metabolite of sibutramine.

Another particular embodiment, the antiadipose agent is orlistate.

Another particular embodiment, the antiadipose agent is mazindol, diethylpropione or phentermine.

Another further particular embodiment, the compounds of the present invention may be administered in combination with one or more antihypertensive active compounds. Examples of antihypertensive active compounds are betablockers such as alprenolol, atenol, timolol, pindolol, propanolol and metoprolol, ACE (angiotensin-converting enzyme) inhibitors such as, for example, benazepril, captopril, enalapril, fosinopril, lisinopril, quinapril and rampril, calcium channel blockers such as nifedipine, felodipine, nicardipine, isradipine, nimodipine, diltiazem and verapamil, and also alphablockers such as doxazosin, urapidil, prazosin and terazosin. Furthermore, reference may be made to Remington: The Science and Practice of Pharmacy, 19th edition, Gennaro, editor, Mack Publishing Co., Easton, Pa., 1995.

The present invention provides for methods for reducing weight in mammals in need thereof, methods for the prophylaxis or treatment of obesity in mammals in need thereof, and methods for the prophylaxis or treatment of type II diabetes in mammals in need thereof, comprising administering to such mammals pharmaceutically effective amounts of compounds of the present invention.

The present invention provides also for methods for reducing weight in mammals in need thereof, methods for the prophylaxis or treatment of obesity in mammals in need thereof, and methods for the prophylaxis or treatment of type II diabetes in mammals in need thereof, comprising administering to such mammals pharmaceutically effective amounts of compounds of the present invention, in combination with pharmaceutically effective amounts of further pharmacologically active compounds suitable for reducing weight in mammals.

It is self-evident that every suitable combination of the compounds of the invention with one or more of the aforementioned compounds and optionally one or more other pharmacologically active substances is to be regarded as covered by the scope of protection of the present invention.

The amount of a compound according to formula (I), i.e. the pharmaceutically effective amount, which is required in order to attain the desired biological effect depends on a number of factors, for example, the specific compound of formula I selected, the intended use, the type of administration and the clinical state of the patient. In general, the daily dose is in the range from 0.3 mg to 100 mg (typically from 3 mg to 50 mg) per day per kilogram of body weight, for example, 3–10 mg/kg/day. An intravenous dose can be, for example, in the range from 0.3 mg to 1.0 mg/kg and can be administered in a suitable manner as an infusion of 10 ng to 100 ng per kilogram per minute. Suitable infusion solutions for these purposes may contain, for example, from 0.1 ng to 10 mg, typically from 1 ng to 10 mg per milliliter. Individual doses may contain, for example, from 1 mg to 10 g of the active compound. Thus, ampules for injections can contain, for example, from 1 mg to 100 mg, and orally administerable individual dose formulations such as, for example, tablets or capsules can contain, for example, from 1.0 to 1000 mg, typically from 10 to 600 mg. In the case of a pharmaceutically acceptable salt, the aforementioned masses relate to the mass of the free base or acid on which the salt is based. The compound used for the prophylaxis or therapy of the abovementioned conditions may be the compounds according to formula (I) themselves, but they are preferably present in the form of a pharmaceutical composition together with an acceptable carrier. The carrier must be naturally acceptable, in the sense that it is compatible with the compound of formula I and is not harmful to the patient's health. The carrier may be a solid or a liquid or both and is preferably formulated with the compound as an individual dose, for example as a tablet which may contain from 0.05% to 95% by weight of the active compound. Further pharmaceutically active substances may also be present, including further compounds according to formula (I). The compounds of the invention may be prepared according to any of the known pharmaceutical methods which essentially comprise mixing the compounds of formula I with pharmacologically acceptable carriers, which may also be termed pharmaceutically acceptable carriers and/or excipients.

Pharmaceutical composition of the invention is one which is suitable for oral, rectal, topical, peroral (e.g. sublingual) and parenteral (e.g. subcutaneous, intramuscular, intradermal or intravenous) administration, although the most suitable manner of administration depends in each individual case on the nature and severity of the condition to be treated and on the nature of the compound according to formula (I) used in each case. Sugar-coated formulations and sugar-coated delayed-release formulations, too, are included within the scope of the invention. Preference is given to acid-resistant and enteric formulations. Suitable enteric coatings include cellulose acetate phthalate, polyvinyl acetate phthalate, hydroxypropylmethylcellulose phthalate, and anionic polymers of methacrylic acid and methyl methacrylate.

Suitable pharmaceutical compositions comprising the compound of formula I for oral administration may be present in separate units as, for example, capsules, cachets, lozenges or tablets, which in each case contain a particular amount of the compound according to formula (I); as powders or granules; as solution or suspension in an aqueous or nonaqueous liquid; or as an oil-in-water or water-in-oil emulsion. As already mentioned, the composition can be prepared according to any suitable pharmaceutical method which includes a step in which the active compound and the carrier (which may comprise one or more additional components) are contacted. In general, the compositions is prepared by uniform and homogeneous mixing of the active compound with a liquid and/or finely dispersed solid carrier, after which the product is shaped, if necessary. Thus, a tablet for example, may be prepared by pressing or shaping a powder or granules of the compound, where appropriate with one or more additional components. Pressed tablets can be prepared by tableting the compound in free-flowing form, for example a powder or granules, mixed, where appropriate, with a binder, lubricant, inert diluent and/or one or more surface active/dispersing agents in a suitable machine. Shaped tablets can be prepared by shaping the pulverulent compound, moistened with an inert liquid diluent, in a suitable machine.

Suitable pharmaceutical compositions for peroral (sublingual) administration include lozenges which contain a compound according to formula (I) with a flavoring, usually sucrose and gum arabic or tragacanth, and pastilles which comprise the compound of formula I in an inert base such as gelatin and glycerol or sucrose and gum arabic.

Suitable pharmaceutical compositions for parenteral administration preferably comprise sterile aqueous preparations of a compound according to formula (I) which are preferably isotonic with the blood of the intended recipient. These preparations are preferably administered intravenously, although they may also be administered subcutaneously, intramuscularly or intradermally as an injection. Said preparations may preferably be prepared by mixing the compound with water and rendering the obtained solution sterile and isotonic with the blood. Injectable compositions of the invention generally contain from 0.1 to 5% by weight of the active compound.

Suitable pharmaceutical compositions for rectal administration are preferably present as individual dose suppositories. These may be prepared by mixing a compound according to formula (I) with one or more conventional solid carriers, for example cocoa butter, and shaping the resulting mixture.

Suitable pharmaceutical compositions for topical application to the skin are preferably present as ointment, cream, lotion, paste, spray, aerosol or oil. Carriers which may be used are petroleum jelly, lanolin, polyethylene glycols, alcohols and combinations of two or more of these substances. In general, the active compound is present at a concentration of from 0.1 to 15%, for example from 0.5 to 2%, by weight of the composition.

Transdermal administration is also possible. Suitable pharmaceutical compositions for transdermal administration may be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is from approx. 1% to 35%, preferably approx. 3% to 15%. A particular possibility is the release of the active compound by electrotransport or iontophoresis, as described, for example, in Pharmaceutical Research, 2(6): 318 (1986).

EXAMPLES

The examples shown below serve to illustrate the invention without limiting it. The melting points or decomposition points (m.p.) measured are uncorrected and generally depend on the heating rate.

The retention times given in the table below refer to the following methods for dermination:

Method A: Column: Merck, LiChroCart 55-2, PuroSpher STAR, RP 18 e; measured at 254 nm; gradient: solvent A acetonitrile/water 90:10+0.5% formic acid; solvent B acetonitrile/water 10:90+0.5% formic acid; flow rate: 0.750 ml/min; time (min)/solvent B (%): 0.00/95.0, 0.50/95.0, 1.75/5.0, 4.25/5.0, 4.50/95.0, 5.00/95.0; temperature: 40° C.:

Method B: column: YMC J'sphere, 33×2, ODS H 80 4 μ; measured at 254 nm; gradient: solvent A acetonitrile+0.5% formic acid; solvent B water+0.5% formic acid; flow rate: 1.00 ml/min; time (min)/solvent B (%): 0.00/90.0, 2.50/5.0, 3.30/5.0, 3.35/90.0; temperature: 30° C.:

compounds are suitable for the prophylaxis and, in particular, for the treatment of problems of excess weight or obesity. The compounds are furthermore suitable for the prophylaxis and, in particular, for the treatment of type II diabetes, of arteriosclerosis and for the normalization of lipid metabolism and for the treatment of high blood pressure.

In a further aspect of the invention, the compounds of the formula I may be administered in combination with one or more further pharmacologically active substances which may be selected, for example, from the group consisting of antidiabetics, antiadipose agents, blood-pressure-lowering active compounds, lipid reducers and active compounds for the treatment and/or prevention of complications caused by diabetes or associated with diabetes.

Suitable antidiabetics include insulins, amylin, GLP-1 and GLP-2 derivatives such as, for example, those disclosed by Novo Nordisk A/S in WO 98/08871 and also oral hypoglycemic active compounds.

Said oral hypoglycemic active compounds preferably include sulfonyl ureas, biguanides, meglitinides, oxadiazolidinediones, thiazolidinediones, glucosidase inhibitors, glucagon receptor antagonists, GLP-1 agonists, potassium channel openers such as, for example, those disclosed by Novo Nordisk A/S in WO 97/26265 and WO 99/03861, insulin sensitizers, activators of insulin receptor

TABLE 1

Examples

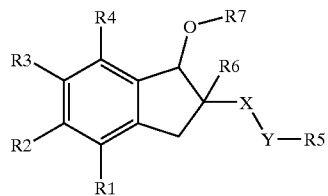

Formula I

| Example | R1 | R2 | R3 | R4 | X | Y | R5 | R6 | R7 | m.p. [° C.] |
|---|---|---|---|---|---|---|---|---|---|---|
| 1 | H | Cl | H | H | $SO_2$ | — | $CH_3$ | F | H | 101 |
|  |  |  |  |  |  |  |  |  |  | retention time in min (method A or B) |
| 2 | H | $CF_3$ | H | H | $SO_2$ | — | $CH_3$ | F | H | 2.041 (B) |
| 3 | H | H | H | H | S | — | $C_6H_4$-4-Cl | F | H | 2.594 (B) |
| 4 | H | H | $C_6H_4$-4-$CF_3$ | H | $SO_2$ | — | $CH_3$ | F | H | 2.438 (B) |
| 5 | Br | H | H | H | $SO_2$ | — | $CH_3$ | F | H | 1.934 (B) |

The compounds of the formula I are distinguished by beneficial actions on the metabolism of lipids, and they are particularly suitable for weight reduction and, after weight reduction, for maintaining a reduced weight in mammals and as anorectic agents. The compounds are distinguished by their low toxicity and their few side effects. The compounds may be employed alone or in combination with other weight-reducing or anorectic active compounds. Further anorectic active compounds of this kind are mentioned, for example, in the Rote Liste, Chapter 01 under weight-reducing agents/appetite suppressants, and may also include those active compounds which increase the energy turnover of the organism and thus lead to weight reduction or else those which influence the general metabolism of said organism such that increased calorie intake does not cause an enlargement of the fat depots and a normal calorie intake causes a reduction in the fat depots of said organism. The kinase, inhibitors of liver enzymes involved in the stimulation of gluconeogenesis and/or glycogenolysis, for example glycogen phosphorylase inhibitors, modulators of glucose uptake and glucose elimination, lipid metabolism-modifying compounds such as antihyperlipidemic active compounds and antilipidemic active compounds, for example HMGCoA-reductase inhibitors, inhibitors of cholesterol transport/cholesterol uptake, inhibitors of the reabsorption of bile acid or inhibitors of microsomal triglyceride transfer protein (MTP), compounds which reduce food intake, PPAR and RXR agonists and active compounds which act on the ATP-dependent potassium channel of beta cells.

The preparation of some examples is described in detail below; the other compounds of the formula I were obtained analogously:

Example 1

5-Chloro-2-fluoro-2-methanesulfonylindan-1-ol:

1. 5-Chloro-2-methylsulfanylindan-1-one:

0.98 g (4 mmol) of 2-bromo-5-chloroindan-1-one and 0.42 g (6 mmol) of sodium thiomethoxide are suspended in 5 ml of ethanol, treated in an ultrasonic bath for 30 minutes and then stirred at room temperature for 90 minutes. The reaction mixture is concentrated under reduced pressure and chromatographed on silica gel using toluene/ethyl acetate 10/1. The eluates are concentrated under reduced pressure, giving 0.63 g of 5-chloro-2-methylsulfanylindan-1-one of melting point 90° C.

2. 5-Chloro-2-methanesulfonylindan-1-one:

0.5 g (2.35 mmol) of 5-chloro-2-methylsulfanylindan-1-one is dissolved in 10 ml of methanol; at 0° C., a solution of 4.33 g (7.05 mmol) of $2KHSO_5 \times KHSO_4 \times K_2SO_4$ in 10 ml of water is added dropwise. The mixture is stirred at room temperature for 5 h; the methanol is distilled off and the aqueous residue is extracted with dichloromethane. The organic phase is separated off, dried over $MgSO_4$, filtered and concentrated under reduced pressure. This gives 0.5 g of 5-chloro-2-methanesulfonylindan-1-one of melting point 197° C.

3. 5-Chloro-2-fluoro-2-methanesulfonylindan-1-one:

0.734 g (3 mmol) of 5-chloro-2-methanesulfonylindan-1-one and 1.77 g (5 mmol) of N-fluoro-N'-(chloromethyl)triethylenediamine bis(tetrafluoroborate) are suspended in a mixture of 2.5 ml of water and 7.5 ml of acetonitrile and stirred under reflux for 4 h. The reaction mixture is cooled, concentrated under reduced pressure and purified chromatographically on silica gel using the mobile phase dichloromethane. This gives 5-chloro-2-fluoro-2-methanesulfonylindan-1-one of melting point 150° C.

4. 5-Chloro-2-fluoro-methanesulfonylindan-1-ol:

0.461 g (2 mmol) of 5-chloro-2-fluoro-2-methanesulfonylindan-1-one and 0.095 g (2.5 mmol) of sodium borohydride are suspended in 5 ml of ethanol and then placed in an ultrasonic bath for 90 min. The reaction mixture is then acidified with 2N hydrochloric acid, and water is added. The alcohol is distilled off and the aqueous residue is extracted with dichloromethane. The organic phase is dried over magnesium sulfate, filtered and concentrated under reduced pressure. This gives 5-chloro-2-fluoro-2-methanesulfonylindan-1-ol of melting point 101° C.

The compounds of examples 2–5 are prepared in an analogous manner, in each case from the corresponding 2-substituted indan-1-one.

Experimental

The Activity of the Compounds was Assayed as Follows:

Biological Test Model:

The anorectic action was tested on female NMRI mice. After removal of feed for 24 hours, the preparation to be tested was administered intraperitoneally (ip) or by gavage (po). The animals were housed singly and, with free access to drinking water, they were offered evaporated milk 30 minutes after administration of the preparation. The consumption of evaporated milk was determined and the general behavior of the animals was monitored every half an hour for 7 hours. The measured milk consumption was compared to that of vehicle-treated control animals.

TABLE 2

Anorectic action, measured as a reduction in the cumulative milk consumption by treated animals compared with control animals

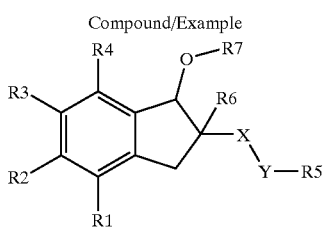

Formula I

| Compound/Example | Dose [mg/kg] | Number of animals/ cumulative milk consumption by treated animals N/[ml] | Number of animals/ cumulative milk consumption by untreated control animals N/[ml] | Reduction in cumulative milk consumption as % of the control |
|---|---|---|---|---|
| Example 1 | 20 | 5/2.06 | 5/3.82 | 46 |

The table indicates that the compounds of the formula I exhibit very good anorectic action.

We claim:

1. A compound of formula I,

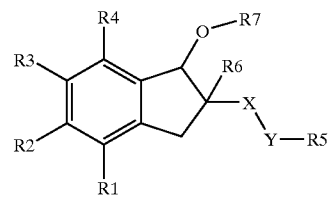

in which $R_1$, $R_2$, $R_3$, $R_4$ are each independently selected from the group consisting of H, F, Cl, Br, I, —CN; $N_3$, —$NO_2$, —OH, —O($C_1$-$C_8$)-alkyl, —O($C_3$-$C_8$)-cycloalkyl, —O—$CH_2$-phenyl, —O—phenyl, —O—CO—($C_1$-$C_8$)-alkyl, —O—CO—($C_3$-$C_8$)-cycloalkyl, —S(O)$_{0-2}$($C_1$-$C_8$)-alkyl, —S(O)$_{0-2}$($C_3$-$C_8$)-cycloalkyl, —$NH_2$, —NH—($C_1C_8$)-alkyl, —NH—($C_3$-$C_8$)-cycloalkyl, —N[($C_1$-$C_8$)-alkyl]$_2$, —N[($C_3$-$C_8$)-cycloalkyl]$_2$, —NH—CO—($C_1$-$C_8$)-alkyl, —NH—CO—($C_3$-$C_8$)-cycloalkyl, —$SO_3H$, —$SO_2$—$NH_2$, —$SO_2$—NH—($C_1$-$C_8$)-alkyl, —$SO_2$—NH—($C_3$-$C_8$)-cycloalkyl, —NH—$SO_2$—$NH_2$, —NH—$SO_2$—($C_1$-$C_8$)-alkyl, —NH—$SO_2$—($C_3$-$C_8$)-cycloalkyl, —O—$CH_2$—COOH, —O—$CH_2$—CO—O($C_1$-$C_8$)-alkyl, —COOH, —CO—O($C_1$-$C_8$)-alkyl, —CO—O—($C_3$-$C_8$)-cycloalkyl, —CO—$NH_2$, —CO—NH($C_1$–$C_8$)-alkyl, —CO—N[($C_1$–$C_8$)-alkyl]$_2$, —($C_1$–$C_8$)-alkyl, —($C_3$–$C_8$)cycloalkyl, —($C_2$–$C_8$)-alkenyl, and —($C_2$–$C_8$)-alkynyl wherein,
the alkyl, alkenyl and alkynyl groups in each case one to seven hydrogen atoms which are optionally replaced by fluorine or one hydrogen is optionally replaced by —OH, —OC(O)$CH_3$, —O—$CH_2$-Ph, —$NH_2$, —NH—CO—$CH_3$, or —N(COO$CH_2$Ph)$_2$,
an aryl group wherein,
the aryl group is phenyl, or 1- or 2-naphthyl, or a heterocycle wherein,
the heterocycle is 5-tetrazolyl,
1-[($C_1$–$C_6$)-alkyl]-5-tetrazolyl,
2-[($C_1$–$C_6$)-alkyl]-5-tetrazolyl,
1-imidazolyl,
1- or 4-[1,2,4]-triazolyl,
2- or 3-thienyl,
2- or 3-furyl,
2-, 3- or 4-pyridyl,
2-, 4- or 5-oxazolyl,
3-, 4- or 5-isoxazolyl,
2-, 4- or 5-thiazolyl, or
3-, 4- or 5-isothiazolyl;
wherein the aryl group or heterocycle is optionally substituted up to two times by F, Cl, Br, —CN, —OH, ($C_1$–$C_4$)-alkyl, —$CF_3$, —O—($C_1$–$C_4$)-alkyl, —S(O)$_{0-2}$($C_1$–$C_6$)-alkyl, —$NH_2$, —NH—$SO_2$—($C_1$–$C_4$)-alkyl, —COOH, —CO—O—($C_1$–$C_4$)-alkyl, or —CO—$NH_2$, and wherein,
the alkyl groups one to seven hydrogen atoms which is optionally replaced by fluorine;
X is S, —SO, or —$SO_2$;
Y is —($CH_2$)$_p$, wherein p is 0–3;
$R_5$ is —$CF_3$, —($C_1$–$C_{18}$)-alkyl, —($C_3$–$C_4$)-cycloalkyl, or ($C_6$–$C_8$)-cycloalkyl, wherein the alkyl groups one to seven hydrogen atoms which is optionally replaced by fluorine;
—($CH_2$)$_r$—CO$R_{16}$, wherein, r is 1–6 and $R_{16}$ is —OH, —O—($C_1$–$C_6$)-alkyl or —$NH_2$, —$CH_2$—CH(NH$R_{13}$)—CO$R_8$, wherein, $R_{13}$ is H or —C(O)—($C_1$–$C_4$)-alkyl and $R_8$ is —OH, —O—($C_1$–$C_6$)-alkyl or —$NH_2$, phenyl, 1- or 2-naphthyl, biphenyl or a heterocyclic radical, wherein the rings or ring systems of the phenyl, 1- or 2-naphthyl or heterocyclic radical are optionally substituted up to two times by F, Cl, Br, I, —CN, —OH, —O($C_1$–$C_8$)-alkyl, —O($C_3$–$C_8$)-cycloalkyl, —O—CO—($C_1$–$C_8$)-alkyl, —O—CO—($C_3$–$C_8$)-cycloalkyl, —S(O)$_{0-2}$($C_1$–$C_8$)-alkyl, —S(O)$_{0-2}$($C_3$–$C_8$)-cycloalkyl, —$NH_2$, —NH—($C_1$–$C_8$)-alkyl, —NH—($C_3$–$C_8$)-cycloalkyl, —NH—CO—($C_3$–$C_8$)-cycloalkyl, —$SO_3$H, —$SO_2$—$NH_2$, —$SO_2$—NH—($C_1$–$C_8$)-alkyl, —$SO_2$—NH—($C_3$–$C_8$)-cycloalkyl, —NH—$SO_2$—$NH_2$, —NH—$SO_2$—($C_1$–$C_8$)-alkyl, —NH—$SO_2$—($C_3$–$C_8$)-cycloalkyl, —O—$CH_2$—COOH, —O—$CH_2$—CO—O($C_1$–$C_8$)-alkyl, —COOH, —CO—O($C_1$–$C_8$)-alkyl, —CO—O—($C_3$–$C_8$)-cycloalkyl, —CO—$NH_2$, —CO—NH($C_1$–$C_8$)-alkyl, —CO—N[($C_1$–$C_8$)-alkyl]$_2$, —($C_1$–$C_8$)-alkyl, or —($C_3$–$C_8$)-cycloalkyl, wherein, the alkyl groups in each case one to seven hydrogen atoms is optionally replaced by fluorine;
$R_6$ is F, Cl, Br, —CN, —$CF_3$, —($C_1$–$C_{18}$)-alkyl, or —($C_3$–$C_8$)-cycloalkyl wherein the alkyl groups one to seven hydrogen atoms is optionally replaced by fluorine,
—($CH_2$)$_s$—CH(NH$R_9$)—CO$R_{10}$ wherein s is 1–6 and $R_9$ is H or —C(O)—($C_1$–$C_6$)-alkyl, and wherein $R_{10}$ is —OH, —O—($C_1$–$C_6$)-alkyl or —C(O)—($C_1$–$C_6$)-alkyl, and wherein $R_{10}$ is —OH, —O—($C_1$–$C_6$)-alkyl or
—$NH_2$, —($CH_2$)$_u$-aryl or —($CH_2$)$_u$-heteroaryl wherein, u is 0–6 and aryl is phenyl, 1- or 2-naphthyl or biphenyl and the aryl or heteroaryl ring is unsubstituted or substituted by at least one and up to two substituents chosen from F, Cl, Br, I, —CN, —OH, —O($C_1$–$C_8$)-alkyl, and —O—CO—($C_1$–$C_8$)-alkyl wherein,
the alkyl radicals one to seven hydrogen atoms is optionally replaced by fluorine, —S(O)$_{0-2}$($C_1$–$C_8$)-alkyl, —$NH_2$, —NH—($C_1$–$C_8$)-alkyl, —NH—CO—($C_1$–$C_8$)-alkyl, —$SO_3$H, —$SO_2$—$NH_2$, —$SO_2$—NH—($C_1$–$C_8$)-alkyl, —NH—$SO_2$—($C_1$–$C_8$)-alkyl, —O—$CH_2$—COOH, —O—$CH_2$—CO—O($C_1$–$C_8$)-alkyl, —COOH, —CO—O($C_1$–$C_8$)-alkyl, —CO—$NH_2$, or ($C_1$–$C_8$)-alkyl, wherein,
the alkyl groups one to seven hydrogen atoms is optionally replaced by fluorine; and
$R_7$ is H;
provided that $R_1$, $R_2$, $R_3$ and $R_4$ are not concurrently H; and
further provided that when $R_1$ and $R_4$ are H, and only one of $R_2$ or $R_3$ is —O-phenyl or —NH—$SO_2$—($C_1$–$C_8$)-alkyl, then the other of $R_2$ or $R_3$ is other than —O-phenyl or —NH—$SO_2$—($C_1$–$C_8$)-alkyl;
or a pharmaceutically acceptable salt or physiologically functional derivative thereof.

2. A compound of formula I,

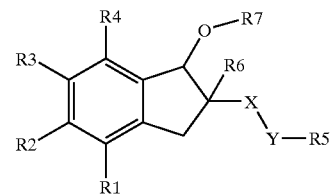

I in which
$R_1$, $R_2$, $R_3$, $R_4$ are each independently selected from the group consisting of H, F, Cl, Br, I, —CN; $N_3$, —$CF_3$, —$NO_2$, —OH, —O($C_1$–$C_8$)-alkyl, —O($C_3$–$C_8$)-cycloalkyl, —O—$CH_2$-phenyl, —O-phenyl, —O—CO—($C_1$–$C_8$)-alkyl, —O—CO—($C_3$–$C_8$)-cycloalkyl, —S(O)$_{0-2}$($C_1$–$C_8$)-alkyl, —S(O)$_{0-2}$($C_3$–$C_8$)-cycloalkyl, —$NH_2$, —NH—($C_1$–$C_8$)-alkyl, —NH—($C_3$–$C_8$)-cycloalkyl, —N[($C_1$–$C_8$)-alkyl]$_2$, —N[($C_3$–$C_8$)-cycloalkyl]$_2$, —NH—CO—($C_1$–$C_8$)-alkyl, —NH—CO—($C_3$–$C_8$)-cycloalkyl, —$SO_3$H, —$SO_2$—$NH_2$, —$SO_2$—NH—($C_1$–$C_8$)-alkyl, —$SO_2$—NH—($C_3$–$C_8$)-cycloalkyl, —NH—$SO_2$—$NH_2$, —NH—$SO_2$—($C_1$–$C_8$)-alkyl, —NH—$SO_2$—($C_3$–$C_8$)-cycloalkyl, —O—$CH_2$—COOH, —O—$CH_2$—CO—O($C_1$–$C_8$)-alkyl, —COOH, —CO—O($C_1$–$C_8$)-alkyl, —CO—O—($C_3$–$C_8$)-cycloalkyl, —CO—$NH_2$, —CO—NH($C_1$–$C_8$)-alkyl, —CO—N [($C_1$–$C_8$)-alkyl]$_2$, —($C_1$–$C_8$)-alkyl, —($C_3$–$C_8$)cycloalkyl, —($C_2$–$C_8$)-alkenyl, and —($C_2$–$C_8$)-alkynyl wherein,
the alkyl, alkenyl and alkynyl groups in each case one to seven hydrogen atoms which is optionally replaced by fluorine or one hydrogen is optionally replaced by —OH, —OC(O)$CH_3$, —O—$CH_2$-Ph, —$NH_2$, —NH—CO—$CH_3$, or —N(COO$CH_2$Ph) 2, an aryl group wherein,
the aryl group is phenyl, or 1- or 2-naphthyl, or a heterocycle wherein,
the heterocycle is 5-tetrazolyl,
1-[($C_1$–$C_6$)-alkyl]-5-tetrazolyl,
2-[($C_1$–$C_6$)-alkyl]-5-tetrazolyl,
1-imidazolyl,
1- or 4-[1,2,4]-triazolyl,
2- or 3-thienyl,
2- or 3-furyl,
2-, 3- or 4-pyridyl,
2-, 4- or 5-oxazolyl,
3-, 4- or 5-isoxazolyl,
2-, 4- or 5-thiazolyl,
3-, 4- or 5-isothiazolyl,
wherein the aryl group or heterocycle is optionally substituted up to two times by F, Cl, Br, —CN, —OH, ($C_1$–$C_4$)-alkyl, —$CF_3$, —O—($C_1$–$C_4$)-alkyl, —S(O)$_{0-2}$($C_1$–$C_6$)-alkyl, —$NH_2$, —NH—$SO_2$—($C_1$–$C_4$)-alkyl, —COOH, —CO—O—($C_1$–$C_4$)-alkyl, or —CO—$NH_2$, and wherein,
the alkyl groups one to seven hydrogen atoms which is optionally replaced by fluorine;
X is S, —SO, or —$SO_2$;
Y is —$(CH_2)_p$, wherein p is 0–3;
$R_5$ is —$CF_3$, —($C_1$–$C_{18}$)-alkyl, —($C_3$–$C_4$)-cycloalkyl, or ($C_6$–$C_8$)-cycloalkyl, wherein
the alkyl groups one to seven hydrogen atoms which is optionally replaced by fluorine,
—$(CH_2)_r$—$COR_{16}$, wherein, r is 1–6 and $R_{16}$ is —OH, —O—($C_1$–$C_6$)-alkyl or —$NH_2$, —$CH_2$—CH(NHR$_{13}$)—$COR_8$, wherein, $R_{13}$ is H or —C(O)—($C_1$–$C_4$)-alkyl and $R_8$ is —OH, —O—($C_1$–$C_6$)-alkyl or —$NH_2$,
phenyl, 1- or 2-naphthyl, biphenyl or a heterocyclic radical, wherein the rings or ring systems of the phenyl, 1- or 2-naphthyl or heterocyclic radical is optionally substituted up to two times by F, Cl, Br, I, —CN, —OH, —O($C_1$–$C_8$)-alkyl, —O($C_3$–$C_8$)-cycloalkyl, —O—CO—($C_1$–$C_8$)-alkyl, —O—CO—($C_3$–$C_8$)-cycloalkyl, —S(O)$_{0-2}$($C_1$–$C_8$)-alkyl, —S(O)$_{0-2}$($C_3$–$C_8$)-cycloalkyl, —$NH_2$, —NH—($C_1$–$C_8$)-alkyl, —NH—($C_3$–$C_8$)-cycloalkyl, —NH—CO—($C_3$–$C_8$)-cycloalkyl, —$SO_3$H, —$SO_2$—$NH_2$, —$SO_2$—NH—($C_1$–$C_8$)-alkyl, —$SO_2$—NH—($C_3$–$C_8$)-cycloalkyl, —NH—$SO_2$—$NH_2$, —NH—$SO_2$—($C_1$–$C_8$)-alkyl, —NH—$SO_2$—($C_3$–$C_8$)-cycloalkyl, —O—$CH_2$—COOH, —O—$CH_2$—CO—O($C_1$–$C_8$)-alkyl, —COOH, —CO—O($C_1$–$C_8$)-alkyl, —CO—O—($C_3$–$C_8$)-cycloalkyl, —CO—$NH_2$, —CO—NH($C_1$–$C_8$)-alkyl, —CO—N[($C_1$–$C_8$)-alkyl]$_2$, —($C_1$–$C_8$)-alkyl, or —($C_3$–$C_8$)-cycloalkyl, wherein,
the alkyl groups in each case one to seven hydrogen atoms is optionally replaced by fluorine;
$R_6$ is F, Cl, Br, —CN, —$CF_3$, —($C_1$–$C_{18}$)-alkyl, or —($C_3$–$C_8$)-cycloalkyl wherein,
the alkyl groups one to seven hydrogen atoms is optionally replaced by fluorine, —$(CH_2)_s$—CH(NHR$_9$)—$COR_{10}$ wherein s is 1–6 and $R_9$ is H or —C(O)—($C_1$–$C_6$)-alkyl, and wherein $R_{10}$ is —OH, —O—($C_1$–$C_6$)-alkyl or —C(O)—($C_1$–$C_6$)-alkyl, and wherein $R_{10}$ is —OH, —O—($C_1$–$C_6$)-alkyl or —$NH_2$, —$(CH_2)_u$-aryl or —$(CH_2)_u$-heteroaryl wherein, u is 0–6 and aryl is phenyl, 1- or 2-naphthyl or biphenyl and the aryl or heteroaryl ring is unsubstituted or substituted by at least one and up to two substituents chosen from F, Cl, Br, I, —CN, —OH, —O($C_1$–$C_8$)-alkyl, and —O—CO—($C_1$–$C_8$)-alkyl wherein,
the alkyl radicals one to seven hydrogen atoms is optionally replaced by fluorine, —S(O)$_{0-2}$($C_1$–$C_8$)-alkyl, —$NH_2$, —NH—($C_1$–$C_8$)-alkyl, —NH—CO—($C_3$–$C_8$)-alkyl, —$SO_3$H, —$SO_2$—$NH_2$, —$SO_2$—NH—($C_1$–$C_8$)-alkyl, —NH—$SO_2$—($C_1$–$C_8$)-alkyl, —O—$CH_2$—COOH, —O—$CH_2$—CO—O($C_1$–$C_8$)-alkyl, —COOR, —CO—O ($C_1$–$C_8$)-alkyl, —CO—$NH_2$, or ($C_1$–$C_8$)-alkyl, wherein,
the alkyl groups one to seven hydrogen atoms is optionally replaced by fluorine; and
$R_7$ is H;
provided that $R_1$, $R_2$, $R_3$ and $R_4$ are not concurrently H; and
further provided that when $R_1$ and $R_4$ are H, and only one of $R_2$ or $R_3$ is —O—phenyl or —NH—$SO_2$—($C_1$–$C_8$)-alkyl, then the other of $R_2$ or $R_3$ is other than —O-phenyl or —NH—$SO_2$—($C_1$–$C_8$)-alkyl;
or a pharmaceutically acceptable salt or physiologically functional derivative thereof.

3. The compound according to claim 1, wherein
$R_1$, $R_2$, $R_3$, $R_4$ are each independently selected from the group consisting of H, F, Cl, Br, I, —CN, $N_3$, —$CF_3$, —$NO_2$, —OH, —O($C_1$–$C_8$)-alkyl, —O($C_3$–$C_8$)-cycloalkyl, —O—$CH_2$-phenyl, —O-phenyl, —O—CO—($C_1$–$C_8$)-alkyl, —O—CO—($C_3$–$C_8$)-cycloalkyl, —S(O)$_{0-2}$($C_1$–$C_8$)-alkyl, —S(O)$_{0-2}$($C_3$–$C_8$)-cycloalkyl, —$NH_2$, —NH—($C_1$–$C_8$)-alkyl, —NH—($C_3$–$C_8$)-cycloalkyl, —N[($C_1$–$C_8$)-alkyl]$_2$, —N[($C_3$–$C_8$)-cycloalkyl]$_2$, —NH—CO—($C_1$–$C_8$)-alkyl, —NH—CO—($C_3$–$C_8$)-cycloalkyl, —$SO_3$H, —$SO_2$—$NH_2$, —$SO_2$—NH—($C_1$–$C_8$)-alkyl, —$SO_2$—NH—($C_3$–$C_8$)-cycloalkyl, —NH—$SO_2$—$NH_2$, —NH—$SO_2$—($C_1$–$C_8$)-alkyl, —NH—$SO_2$—($C_3$–$C_8$)-cycloalkyl, —O—$CH_2$—COOH, —O—$CH_2$—CO—O($C_1$–$C_8$)-alkyl, —COOH, —CO—O($C_1$–$C_8$)-alkyl, —CO—O—($C_3$–$C_8$)-cycloalkyl, —CO—$NH_2$, —CO—NH($C_1$–$C_8$)-alkyl, —CO—N[($C_1$–$C_8$)-alkyl]$_2$, —($C_1$–$C_8$)-alkyl, —($C_3$–$C_8$)cycloalkyl, —($C_2$–$C_8$)-alkenyl, and —($C_2$–$C_8$)-alkynyl wherein,
the alkyl, alkenyl and alkynyl groups in each case one to seven hydrogen atoms is optionally replaced by fluorine, or one hydrogen may be replaced by —OH, —OC(O)$CH_3$, —O—$CH_2$-Ph, —$NH_2$, —NH—CO—$CH_3$, or —N(COOCH$_2$Ph)$_2$,
an aryl group wherein,
the aryl group is phenyl, or 1- or 2-naphthyl, or a heterocycle wherein,
the heterocycle is 5-tetrazolyl,
1-[($C_1$–$C_6$)-alkyl]-5-tetrazolyl,
2-[($C_1$–$C_6$)-alkyl]-5-tetrazolyl,
1-imidazolyl,
1- or 4-[1,2,4]-triazolyl,
2- or 3-thienyl,
2- or 3-furyl,
2-, 3- or 4-pyridyl,
2-, 4- or 5-oxazolyl,
3-, 4- or 5-isoxazolyl,
2-, 4- or 5-thiazolyl,
3-, 4- or 5-isothiazolyl,
wherein, the aryl group or heterocycle is optionally substituted up to two times by F, Cl, Br, —CN, —OH, $(C_1-C_4)$-alkyl, —$CF_3$, —O—$(C_1-C_4)$-alkyl, —$S(O)_{0-2}(C_1-C_6)$-alkyl, —$NH_2$, —NH—$SO_2$—$(C_1-C_4)$-alkyl, —COOH, —CO—O—$(C_1-C_4)$-alkyl, or —CO—$NH_2$, and wherein,
the alkyl groups one to seven hydrogen atoms is optionally replaced by fluorine;

X is S, —SO, or —$SO_2$;

Y is —$(CH_2)_p$, wherein p is 0–3;

$R_5$ is —$CF_3$, —$(C_1-C_{18})$-alkyl, —$(C_3-C_4$ and $C_6-C_8)$-cycloalkyl, wherein,
the alkyl groups one to seven hydrogen atoms is optionally replaced by fluorine,
—$(CH_2)_r$—$COR_{16}$, wherein, r is 1–6 and $R_{16}$ is —OH, —O—$(C_1-C_6)$-alkyl or —$NH_2$,
—$CH_2$—$CH(NHR_{13})$—$COR_8$, wherein, $R_{13}$ is H or —C(O)—$(C_1-C_4)$-alkyl and $R_8$ is —OH, —O—$(C_1-C_6)$-alkyl or —$NH_2$,
phenyl, 1- or 2-naphthyl, biphenyl or a heterocyclic radical, wherein the rings or ring systems of the phenyl, 1- or 2-naphthyl or heterocyclic radical is optionally substituted up to two times by F, Cl, Br, I, —CN, —OH,
—$O(C_1-C_8)$-alkyl, —$O(C_3-C_8)$-cycloalkyl, —O—CO—$(C_1-C_8)$-alkyl, —O—CO—$(C_3-C_8)$-cycloalkyl, —$S(O)_{0-2}(C_1-C_8)$-alkyl, —$S(O)_{0-2}(C_3-C_8)$-cycloalkyl, —$NH_2$, —NH—$(C_1-C_8)$-alkyl, —NH—$(C_3-C_8)$-cycloalkyl, —$N[(C_1-C_8)$-alkyl$]_2$, —$N[(C_3-C_8)$-cycloalkyl$]_2$,
—NH—CO—$(C_2-C_8)$-alkyl, —NH—CO—$(C_3-C_8)$-cycloalkyl —$SO_3H$, —$SO_2$—$NH_2$, —$SO_2$—NH—$(C_1-C_8)$-alkyl, —$SO_2$—NH—$(C_3-C_8)$-cycloalkyl, —NH—$SO_2$—$NH_2$, —NH—$SO_2$—$(C_1-C_8)$-alkyl, —NH—$SO_2$—$(C_3-C_8)$-cycloalkyl, —O—$CH_2$—COOH, —O—$CH_2$—CO—$O(C_1-C_8)$-alkyl, —COOH, —CO—$O(C_1-C_8)$-alkyl, —CO—O—$(C_3-C_8)$-cycloalkyl, —CO—$NH_2$, —CO—NH$(C_1-C_8)$-alkyl, —CO—$N[(C_1-C_8)$-alkyl$]_2$, —$(C_1-C_8)$-alkyl, or —$(C_3-C_8)$-cycloalkyl, wherein, the alkyl groups in each case one to seven hydrogen atoms is optionally replaced by fluorine;

$R_6$ is F, Cl, Br, or —$(C_1-C_{18})$-alkyl, wherein,
the alkyl groups one to seven hydrogen atoms is optionally replaced by fluorine, and $R_7$ is H;

or a pharmaceutically acceptable salt or physiologically functional derivative thereof.

4. The compound according to claim 1, wherein,
$R_1$, $R_2$, $R_3$, $R_4$ are each independently selected from the group consisting of H, F, Cl, Br, —$CF_3$, —$(C_1-C_8)$-alkyl, wherein,
the alkyl groups one to seven hydrogen atoms is optionally replaced by fluorine, and
phenyl, wherein, the phenyl is optionally substituted up to two times by F, Cl, Br, —OH, —$O(C_1-C_8)$-alkyl or —$(C_1-C_8)$-alkyl, and wherein, the alkyl groups in each case one to seven hydrogen atoms is optionally replaced by fluorine;

X is S, or —$SO_2$;

Y is —$(CH_2)_p$, wherein, p is 0 or 1;

$R_5$ is —$CF_3$, —$(C_1-C_{18})$-alkyl, —$(C_3-C_4$ and $C_6-C_8)$-cycloalkyl, wherein,
the alkyl groups one to seven hydrogen atoms is optionally replaced by fluorine, phenyl, wherein, the phenyl is optionally substituted up to two times by F, Cl, Br, —OH, —$O(C_1-C_8)$-alkyl or $(C_1-C_8)$-alkyl, and wherein,
the alkyl groups in each case one to seven hydrogen atoms is optionally replaced by fluorine;

$R_6$ is F, Cl, Br, or —$(C_1-C_{18})$-alkyl wherein,
the alkyl groups one to seven hydrogen atoms is optionally replaced by fluorine; and $R_7$ is H; or a pharmaceutically acceptable salt or physiologically functional derivative thereof.

5. A pharmaceutical composition comprising a pharmaceutically effective amount of a compound according to claim 1 or 2 and a pharmaceutically acceptable carrier.

6. The compound according to claim 1, wherein R2 is —$C_1$-alkyl, and wherein three hydrogens on the alkyl group are replaced by fluorine.

* * * * *